US010980980B2

(12) United States Patent
Ishida

(10) Patent No.: US 10,980,980 B2
(45) Date of Patent: Apr. 20, 2021

(54) CATHETER ASSEMBLY

(71) Applicant: Terumo Kabushiki Kaisha, Tokyo (JP)

(72) Inventor: Masahiro Ishida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 443 days.

(21) Appl. No.: 15/927,456

(22) Filed: Mar. 21, 2018

(65) Prior Publication Data

US 2018/0207406 A1 Jul. 26, 2018

Related U.S. Application Data

(63) Continuation of application No. PCT/JP2016/077712, filed on Sep. 20, 2016.

(30) Foreign Application Priority Data

Sep. 24, 2015 (JP) .............................. JP2015-186542

(51) Int. Cl.
*A61M 25/06* (2006.01)
*A61M 25/09* (2006.01)
(Continued)

(52) U.S. Cl.
CPC ...... *A61M 25/065* (2013.01); *A61M 25/0606* (2013.01); *A61M 25/0631* (2013.01);
(Continued)

(58) Field of Classification Search
CPC ............ A61M 25/065; A61M 25/0631; A61M 25/0606; A61M 25/09041;
(Continued)

(56) References Cited

U.S. PATENT DOCUMENTS 4,205,675 A * 6/1980 Vaillancourt ...... A61M 25/0111
604/164.01
4,326,519 A * 4/1982 D'Alo ............... A61M 25/0637
604/165.04
(Continued)

FOREIGN PATENT DOCUMENTS

JP 58-501856 A 11/1983
JP 2013-529111 A 7/2013
(Continued)

OTHER PUBLICATIONS

International Search Report issued in International Patent Application No. PCT/JP2016/077712 dated Dec. 20, 2016.
(Continued)

*Primary Examiner* — Theodore J Stigell
*Assistant Examiner* — Rachel T. Smith
(74) *Attorney, Agent, or Firm* — Foley & Lardner LLP

(57) ABSTRACT

A catheter assembly includes: a catheter; a hollow inner needle that is removably disposed in the catheter and has a lumen through which a guide wire is insertable; a needle hub that is fixed to a proximal end portion of the inner needle; and a guide member that is attachable to a proximal end portion of the needle hub and configured to guide the guide wire towards the inner needle.

14 Claims, 36 Drawing Sheets

(51) Int. Cl.
   *A61M 25/00* (2006.01)
   *A61M 25/01* (2006.01)
(52) U.S. Cl.
   CPC ............... *A61M 25/09041* (2013.01); *A61M 2025/0008* (2013.01); *A61M 2025/0175* (2013.01); *A61M 2025/09175* (2013.01)
(58) Field of Classification Search
   CPC .. A61M 2025/0008; A61M 2025/0175; A61M 2025/09175
   See application file for complete search history.

(56) References Cited

U.S. PATENT DOCUMENTS 4,417,886 A * 11/1983 Frankhouser ..... A61M 25/0606
   600/435
5,531,713 A * 7/1996 Mastronardi ..... A61M 25/0631
   604/263

FOREIGN PATENT DOCUMENTS

| WO | WO-2014/196050 A1 | 12/2014 |
| WO | WO-2015/115315 A1 | 8/2015 |
| WO | WO-2015/115316 A1 | 8/2015 |

OTHER PUBLICATIONS

Office Action dated Sep. 29, 2020 in corresponding Japanese Patent Application No. 2017-541554.

\* cited by examiner

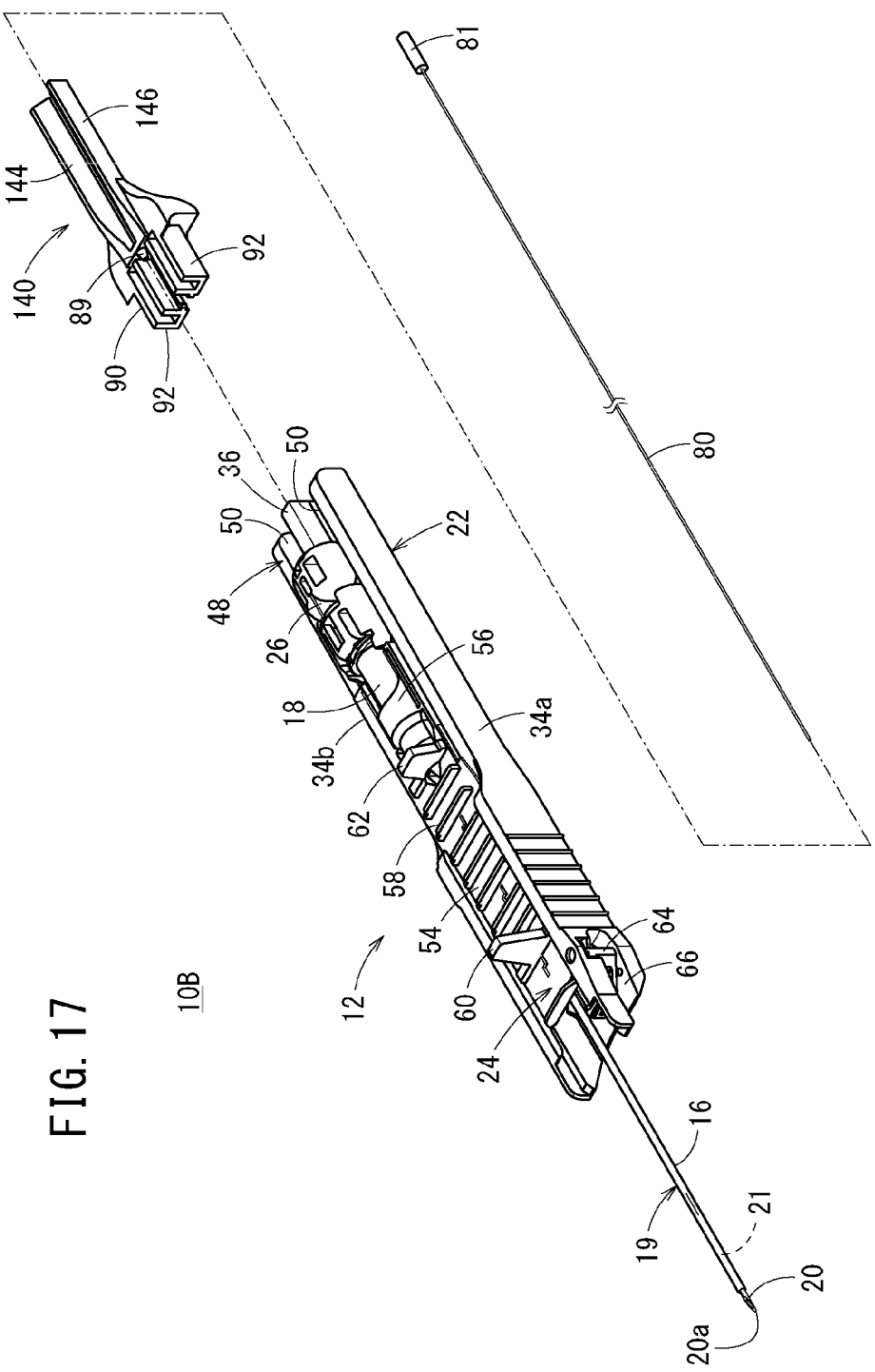

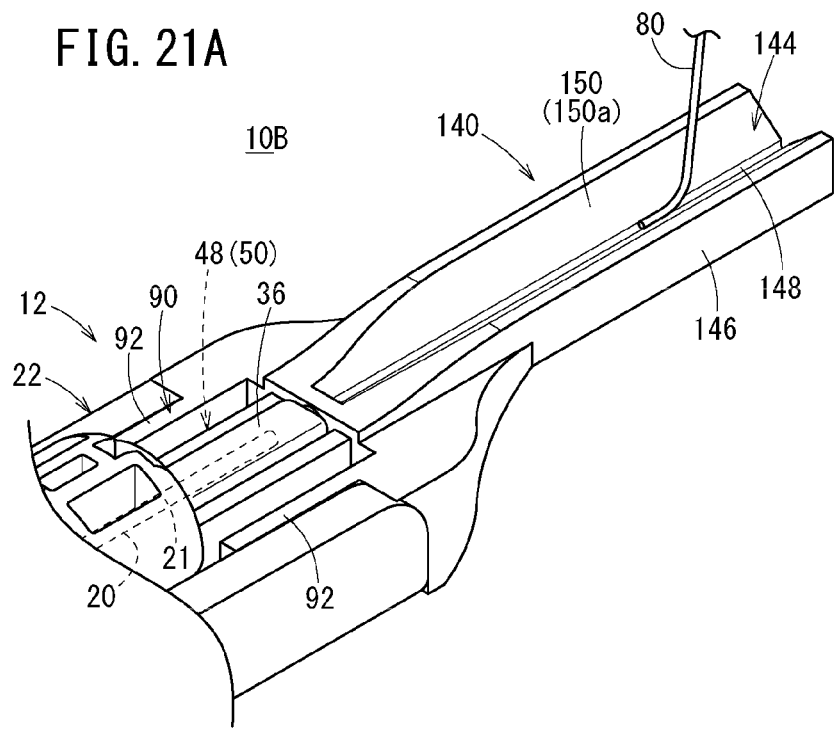
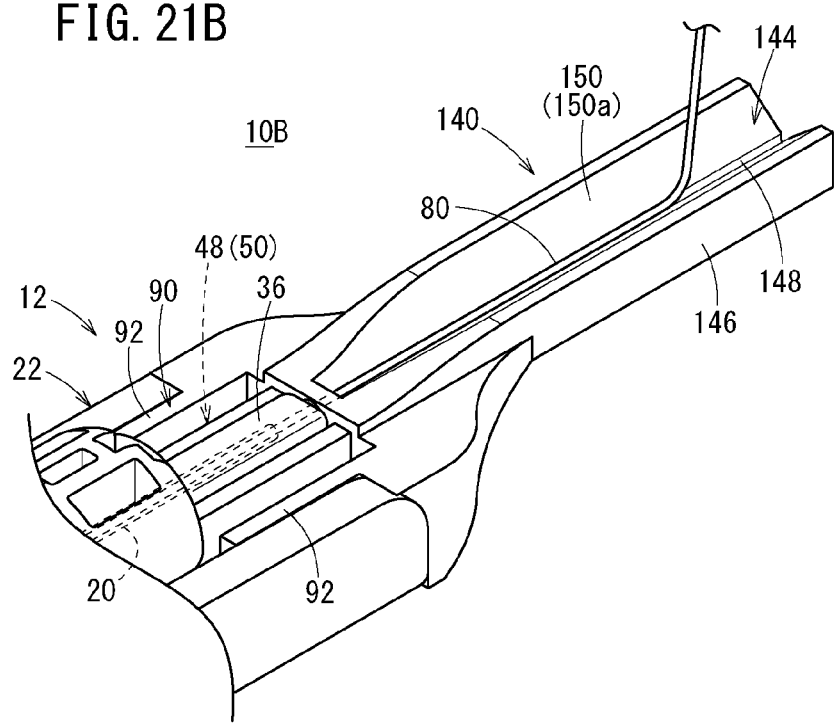

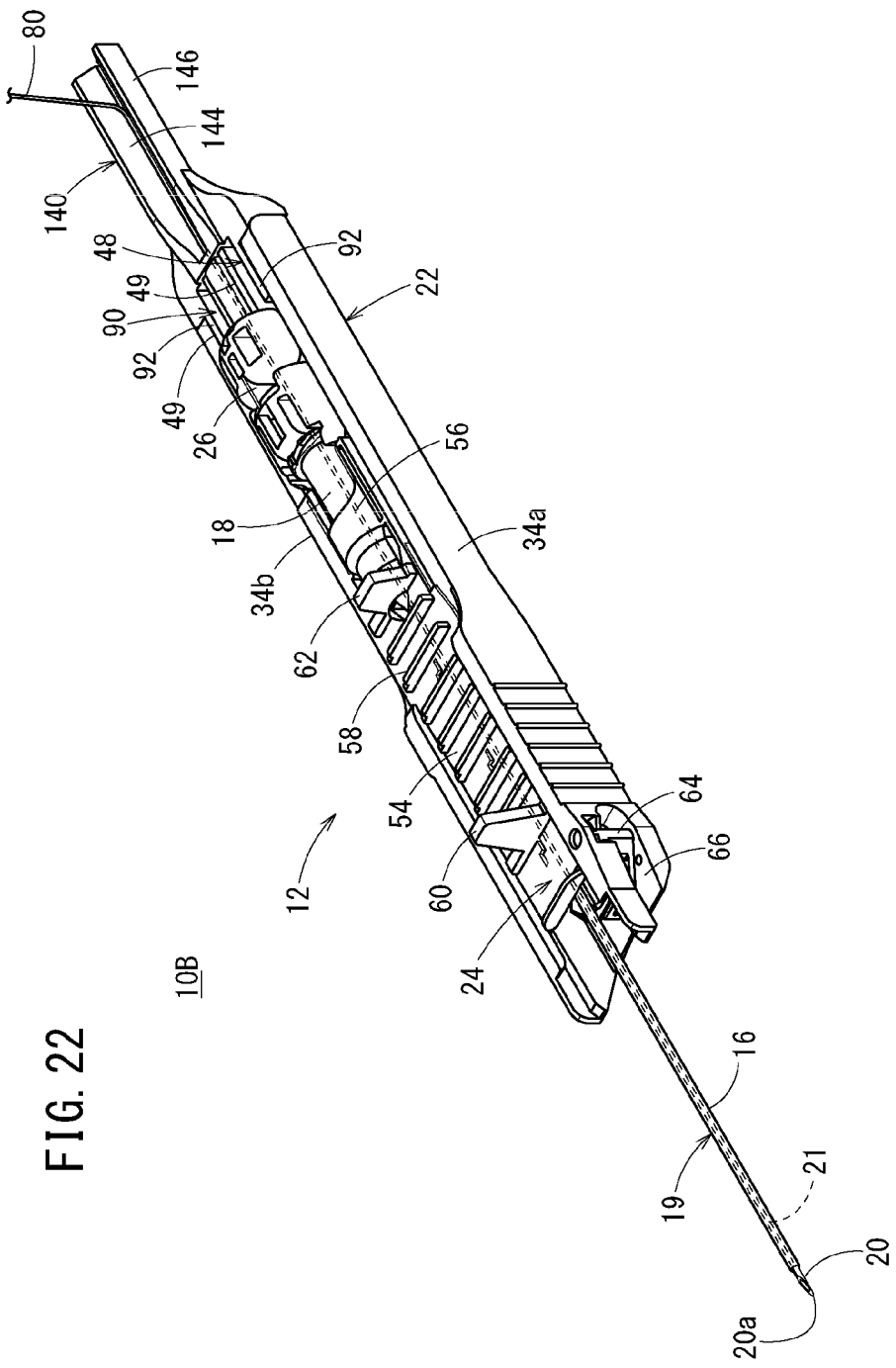

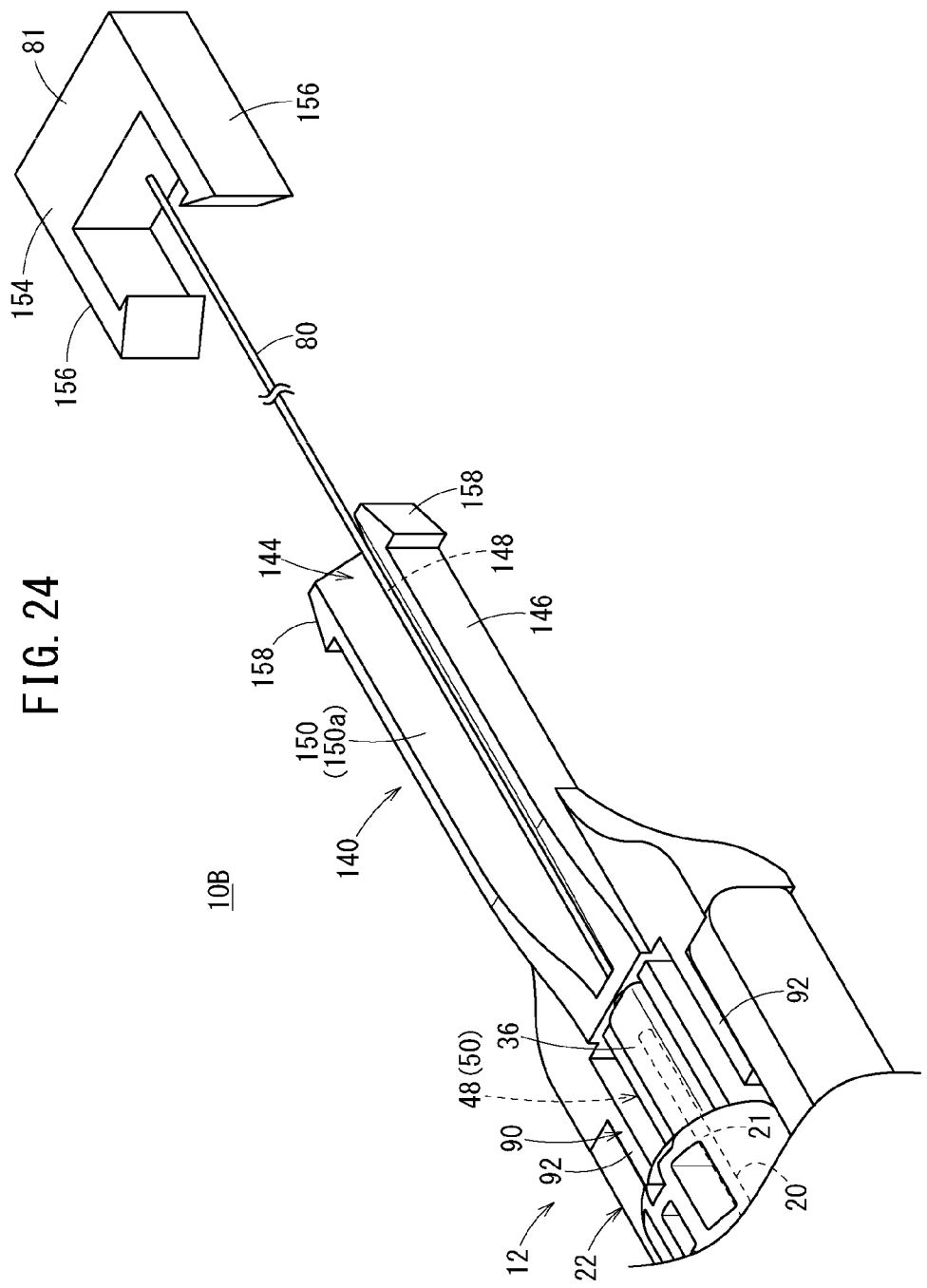

CATHETER ASSEMBLY

CROSS REFERENCE TO RELATED APPLICATIONS

This application is a bypass continuation of PCT Application No. PCT/JP2016/077712, filed on Sep. 20, 2016, which claims priority to Japanese Application No. 2015-186542, filed on Sep. 24, 2015, the contents of both of which are hereby incorporated by reference in their entireties.

BACKGROUND

Technical Field

The present disclosure relates to a catheter assembly configured to puncture and remain indwelled in a blood vessel when performing an infusion or the like to patient, for example.

Background Art

Conventionally, for example, a catheter assembly is used when performing an infusion or the like to a patient. This kind of the catheter assembly includes a hollow catheter, a catheter hub fixed to a proximal end of the catheter, a hollow inner needle that is inserted into the catheter and has a sharp needle tip at a distal end, and a needle hub fixed to a proximal end of the inner needle. In addition, there is a catheter assembly including a guide wire, which is inserted into a lumen of an inner needle to be axially slidable and can protrude from a distal end of the inner needle in order to facilitate insertion of a catheter into a blood vessel, for example, as disclosed in JP 2013-529111 A.

SUMMARY

As described above, the catheter assembly has a first type that does not include the guide wire and a second type that includes the guide wire. In the case of the catheter assembly of the first type, it is advantageous in terms that an operation thereof is simple, the operation is easy to learn, and the device is compact. Incidentally, for most patients among those who need indwelling catheterization, it is possible to use the catheter assembly of the first type, because the indwelling thereof is relatively simple.

On the other hand, in the case of the catheter assembly of the second type, there is an advantage in that the indwelling thereof is easy even for a patient for which indwelling using the first type is difficult. However, there are disadvantages in terms that it is difficult to operate the second type as compared with the first type, the operation is difficult to learn, and the device is large.

In view of the above-described circumstances, an object of certain embodiments of the present disclosure is to provide a catheter assembly that is has the advantages of a catheter assembly that does not include a guide wire when being applied to a patient for which indwelling of a catheter is simple, and enjoying advantages of a catheter assembly that includes the guide wire when being applied to a patient for which the indwelling of the catheter is difficult.

According to one embodiment, a catheter assembly includes: a catheter; a hollow inner needle that is removably inserted into the catheter and has a lumen through which a guide wire is insertable; a needle hub that is fixed to a proximal end portion of the inner needle; and a guide member that is attachable to a proximal end portion of the needle hub and configured to guide the guide wire towards the inner needle.

According to the catheter assembly with the above-described configuration, a guide member and the guide wire are not used when the catheter is indwelled in a patient for which the catheter is likely to be simply indwelled, and thus, the operation thereof is simple, the operation is easy to learn, and the device is also compact. In addition, when the catheter is indwelled in a patient for which the catheter is likely to be hardly indwelled, it is possible to perform smooth indwelling by attaching the guide member to a needle hub and using the guide wire. In this manner, it is possible to enjoy the advantages of both the cases by selecting whether to use the guide wire depending on a situation.

The above-described catheter assembly may further include: the guide wire that is slidably supported on the guide member; and a wire operation member that supports the guide wire, is relatively displaceable in an axial direction with respect to the guide member, and moves the guide wire in the axial direction with respect to the guide member along with displacement.

With this configuration, the guide wire moves forward along with the operation of the wire operation member in the axial direction, and thus, it is possible to insert the guide wire into a blood vessel with a simple operation.

The above-described catheter assembly may further include a cover that is formed in a hollow cylindrical shape so as to cover the guide wire between the guide member and the wire operation member in an initial state, and contracts in the axial direction along with movement of the wire operation member in a distal end direction with respect to the guide member.

With this configuration, the guide wire is covered by the cover in the initial state, and thus, it is possible to inhibit contamination of the guide wire.

In the above-described catheter assembly, the wire operation member may be relatively movable in the axial direction within a regulated range with respect to the cover, and a distal end of the guide wire may be positioned in the lumen of a distal end portion of the inner needle in a state where the guide member is attached to the needle hub, the cover contracts in the axial direction to a maximum extent, and the wire operation member is positioned on a most proximal end side with respect to the cover.

With this configuration, it is possible to easily arrange the distal end of the guide wire at a position (zero protrusion length position) where a protrusion length of the guide wire from the distal end of the inner needle is zero. Therefore, it is possible to puncture a patient with the catheter assembly in the state of the zero protrusion length position, and to effectively insert the guide wire into the blood vessel thereafter.

In the above-described catheter assembly, the wire operation member may be releasably fixed to the cover at a position on the most proximal end side within a movable range with respect to the cover.

With this configuration, it is possible to temporarily fix the distal end of the guide wire to the zero protrusion length position in the state where the cover is contracted in the axial direction, and to effectively suppress the guide wire from protruding from the distal end of the inner needle before puncturing the patient.

In the above-described catheter assembly, the cover may be provided with a lock mechanism that fixes the cover to the guide member when the cover contracts in the axial direction to the maximum extent.

With this configuration, it is possible to inhibit the guide wire from retracting after the distal end of the guide wire has been arranged at the zero protrusion length position.

In the above-described catheter assembly, the cover may have a telescopic structure in which a plurality of tubular members having different sizes is combined so as to be relatively movable in the axial direction.

With this configuration, it is possible to move the wire operation member smoothly in the distal end direction with respect to the guide member. In addition, the cover is shortened in a state after the cover has been contracted, a product in a puncture state becomes compact and easy to puncture.

In the above-described catheter assembly, the guide member may have a guide groove to guide the guide wire toward the lumen of the inner needle, and the guide groove may have a bottom portion extending coaxially with the lumen of the inner needle in a state where the guide member is attached to the needle hub, and an inducing portion that is open on an upper surface of the guide member, is continuous to the bottom portion, and is narrowed in width toward the bottom portion.

With this configuration, when the guide wire is placed in the guide groove, the distal end of the guide wire is induced to the bottom portion by the inducing portion, and the distal end of the guide wire is guided toward the lumen of the inner needle at the bottom portion. Therefore, it is possible to smoothly insert the guide wire into the lumen of the inner needle.

The above-described catheter assembly may further include an excessive insertion inhibition portion that is attached to the guide wire and inhibits excessive insertion of the guide wire by coming into contact with the guide member.

With this configuration, it is possible to inhibit the excessive insertion of the guide wire.

The above-described catheter assembly may further include a retraction inhibition portion that is fixed to the guide wire and inhibits the guide wire from retracting with respect to the needle hub after the guide wire advances such that the guide wire protrudes from the distal end of the inner needle by a predetermined length.

With this configuration, it is possible to inhibit unintentional retraction of the guide wire protruding from the distal end of the inner needle by the predetermined length.

The above-described catheter assembly may further include a cover that covers the guide wire in an initial state.

With this configuration, the guide wire is covered by the cover in the initial state, and thus, it is possible to inhibit contamination of the guide wire.

In the above-described catheter assembly, the cover may be configured to be soft such that a distal end of the cover is compressed by being pushed in a proximal end direction along with insertion of the guide wire into the inner needle via the guide member.

With this configuration, the cover contracts along with the insertion of the guide wire, and thus, it is possible to insert the guide wire without any problem.

In the above-described catheter assembly, a connector, configured to be connectable to the guide member, may be provided at the distal end of the cover, and a distal end of the connector may face the guide groove in a state where the connector is connected to the guide member.

With this configuration, it is possible to easily introduce the distal end of the guide wire into the guide groove by connecting the connector to the guide member to advance the guide wire.

In the above-described catheter assembly, the wire operation member may be supported by the guide member so as to be slidable in the axial direction.

With this configuration, it is possible to easily perform the operation of causing the guide wire to proceed toward the inner needle and the operation of causing the guide wire to protrude from the distal end of the inner needle.

In the above-described catheter assembly, the wire operation member may have a slide portion engaged with the guide member so as to be slidable in the axial direction, and an extension portion extending from the slide portion in the distal end direction, and a most distal end portion of the extension portion may be positioned on a distal end side of a most proximal end portion of the needle hub in a state where the guide member is attached to the needle hub and a distal end of the guide wire is positioned inside a distal end portion of the inner needle.

With this configuration, it is easy to operate the wire operation member.

In the above-described catheter assembly, the guide member may be provided with a guide rail that overlaps the needle hub in the axial direction in a state where the guide member is attached to the needle hub, and slidably supports the extension portion and guides the extension portion in the axial direction.

With this configuration, it is possible to improve stability in straight movement of the wire operation member.

In the above-described catheter assembly, a first fitting portion, which has a plurality of female fitting portions open in a proximal end direction, may be provided at the proximal end portion of the needle hub, and a second fitting portion, which protrudes in the distal end direction and has a plurality of male fitting portions fittable to the plurality of female fitting portions, may be provided at a distal end portion of the guide member.

With this configuration, it is possible to stably attach the guide member to the needle hub.

In the above-described catheter assembly, the needle hub may have left and right sidewalls and a needle holding portion that is provided between the left and right sidewalls and holds the proximal end portion of the inner needle, and the first fitting portion may be formed of the left and right sidewalls and the needle holding portion.

With this configuration, it is possible to easily provide the first fitting portion having the plurality of female fitting portions.

In the above-described catheter assembly, a concave portion extending in the axial direction may be provided on one sidewall surface of the first fitting portion and the second fitting portion, and a convex portion, which is fittable to the concave portion and extends in the axial direction, may be provided on another sidewall surface of the first fitting portion and the second fitting portion.

With this configuration, even when the first fitting portion is open upward, it is possible to suppress shaking of the guide member in a vertical direction with respect to the needle hub due to the fitting action between the concave portion and the convex portion.

In the above-described catheter assembly, one of the first fitting portion and the second fitting portion may be provided with an engagement protrusion that inhibits the guide member from retracting with respect to the needle hub by being engaged with the other one of the first fitting portion and the second fitting portion when the guide member is attached to the needle hub.

With this configuration, it is possible to inhibit the guide member from being unintentionally withdrawn from the needle hub in the proximal end direction after the guide member has been attached to the needle hub.

In the above-described catheter assembly, the needle hub may have a wire introduction hole that communicates with the lumen of the inner needle on the proximal end side of the inner needle and through which the guide wire is insertable, the guide member may have a wire lead-out hole that communicates with the bottom portion on the distal end side of the bottom portion and through which the guide wire is insertable, and one or both of the wire introduction hole and the wire lead-out hole may be formed in a tapered shape that decreases in diameter toward the inner needle.

With this configuration, it is possible to smoothly introduce the guide wire into the lumen of the inner needle.

According to the catheter assembly of certain embodiments described herein, it is possible to enjoy the advantages of the catheter assembly that does not include the guide wire when being applied to the patient for which the indwelling of the catheter is simple, and enjoying the advantages of the catheter assembly that includes the guide wire when being applied to the patient for which the indwelling of the catheter is difficult.

BRIEF DESCRIPTION OF DRAWINGS

FIG. 17 is a perspective view of a catheter assembly according to a second embodiment.

FIG. 21A is a second view for describing the method of using the catheter assembly illustrated in FIG. 17, and FIG. 21B is a third view for describing the method of using the catheter assembly illustrated in FIG. 17.

FIG. 22 is a fourth view for describing the method of using the catheter assembly illustrated in FIG. 17.

FIG. 24 is a perspective view illustrating a modification in which a guide wire is provided with a guide wire retraction inhibition portion.

DESCRIPTION OF EMBODIMENTS

Figure 1:
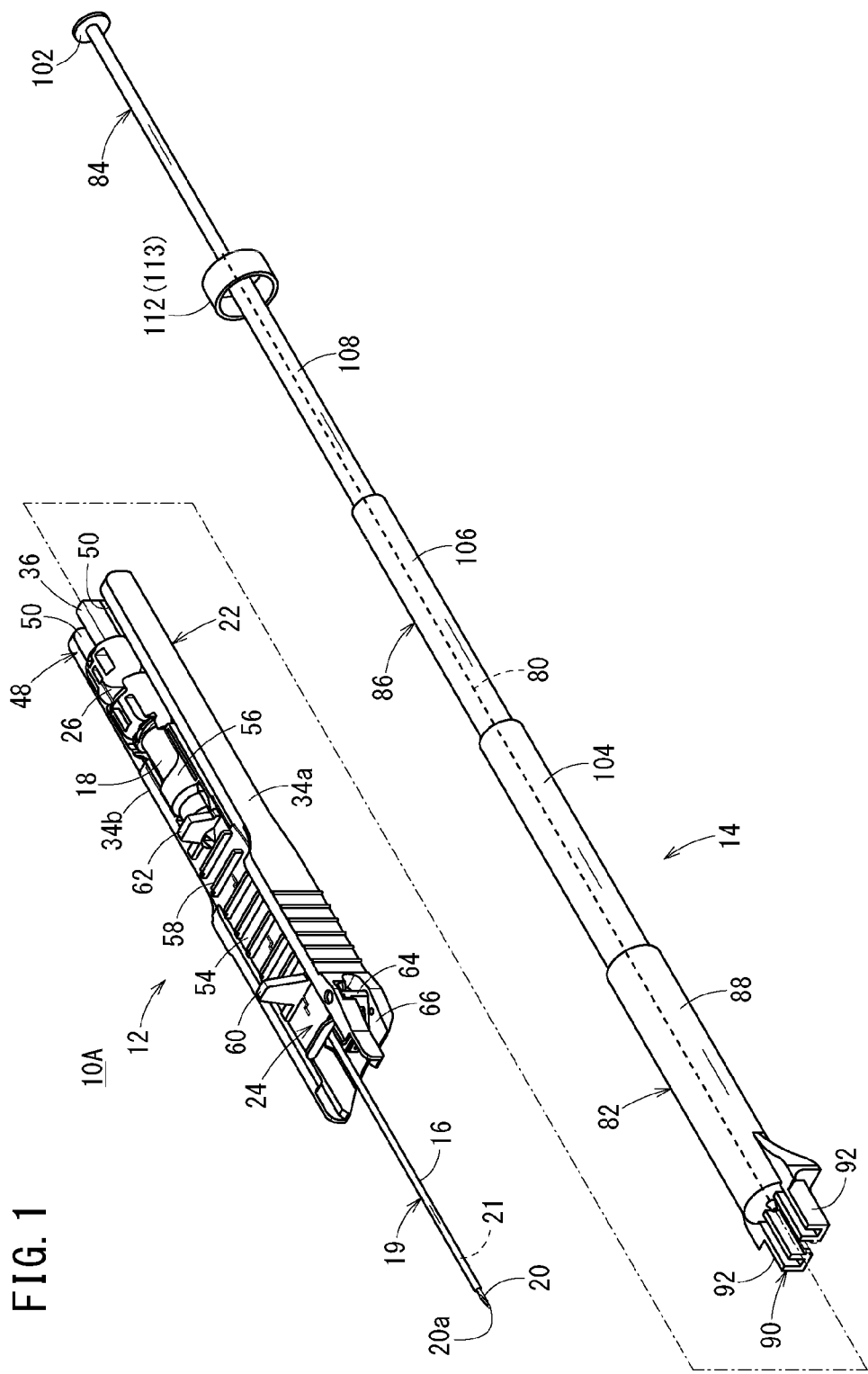
FIG. 1 is a perspective view of a catheter assembly according to a first embodiment.

Hereinafter, a plurality of preferred embodiments of a catheter assembly will be described with reference to the accompanying drawings. Incidentally, the same or similar elements in second and third embodiments and modifications thereof as those of a first embodiment will be denoted by the same reference numerals, and a detailed description thereof will be omitted First Embodiment The catheter assembly 10A illustrating the initial state in FIG. 1 is applied when performing a transfusion, a blood transfusion, and the like to a patient (living body), and constructs an introduction portion of a medicinal liquid or the like by being tapped into the patient's body and indwelled. The catheter assembly 10A may be configured as a catheter 16 (for example, a central venous catheter, a PICC, a mid-line catheter, and the like) having a longer length than a peripheral venous catheter. Incidentally, the catheter assembly 10A may be configured as the peripheral venous catheter. In addition, the catheter assembly 10A is not limited to the venous catheter, and may be configured as an arterial catheter such as a peripheral arterial catheter.

As illustrated in FIG. 1, the catheter assembly 10A includes a catheter unit 12 forming the main part of the catheter assembly 10A and a guide wire unit 14 attachable to the catheter unit 12.

Figure 2:
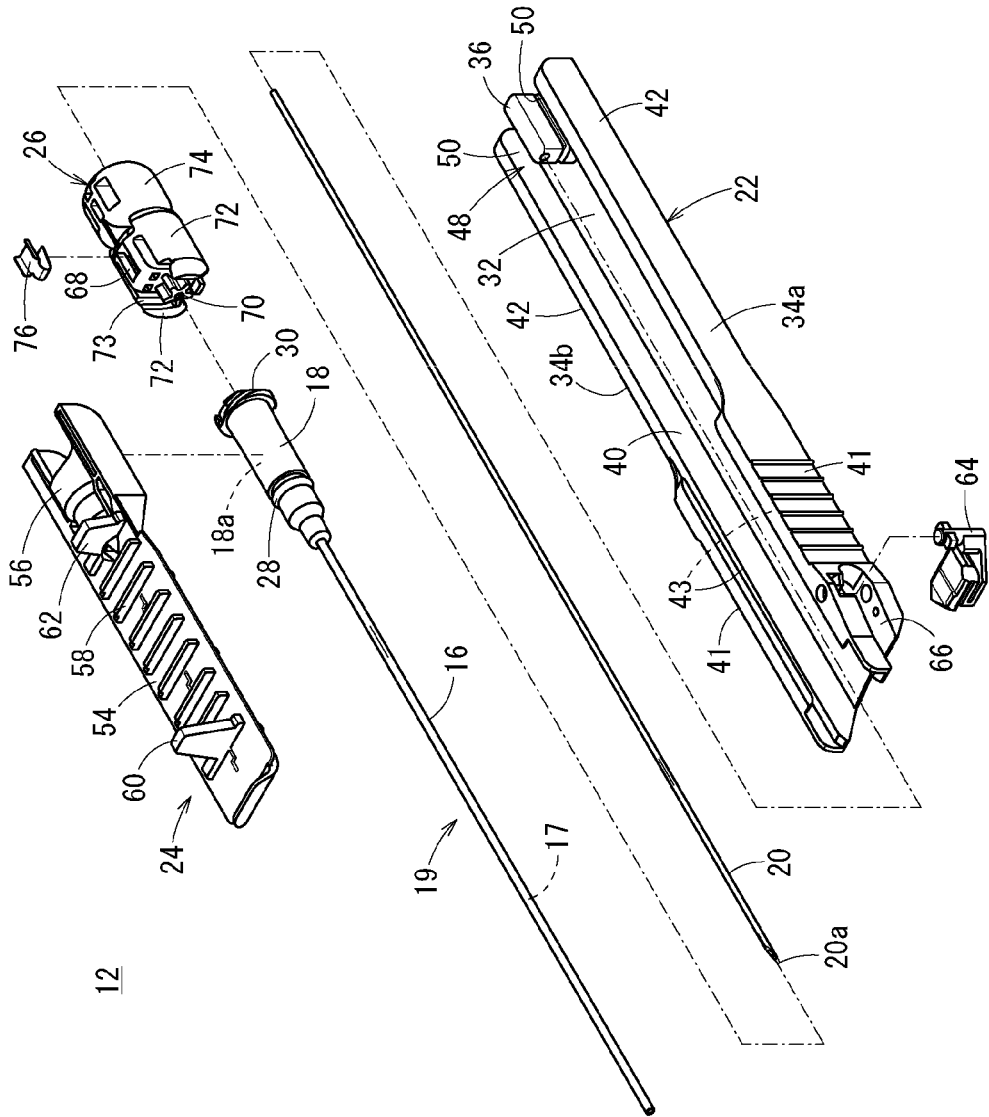
FIG. 2 is an exploded perspective view of a catheter unit.

As illustrated in FIGS. 1 and 2, the catheter unit 12 includes a catheter 16, a catheter hub 18 fixedly holding the catheter 16, a hollow inner needle 20 removably inserted into the catheter 16, a needle hub 22 fixedly holding the inner needle 20, a catheter operation member 24 attached on an upper side of the catheter hub 18, and a needle protection member 26 connected to a proximal end of the catheter hub 18.

The catheter 16 is a narrow tube that is flexible and in which a lumen is formed to penetrate therethrough. A length of the catheter 16 is not particularly limited but can be appropriately designed according to use and various conditions, and is set to, for example, about 14 to 500 mm, about 30 to 400 mm, or about 76 to 200 mm.

A constituent material of the catheter 16 is not particularly limited, but a soft resin material is suitable, and examples thereof include a fluorine-based resin such as polytetrafluoroethylene (PTFE), ethylene-tetrafluoroethylene copolymer (ETFE) and perfluoroalkoxy fluorine resin (PFA), an olefin-based resin such as polyethylene and polypropylene or a mixture thereof, polyurethane, polyester, polyamide, polyether nylon resin, a mixture of the olefin-based resin and ethylene-vinyl acetate copolymer, and the like.

A proximal end portion of the catheter 16 is fixed to a distal end portion inside the catheter hub 18 by an appropriate fixing method (crimping, fusion, adhesion, or the like). The catheter 16 and the catheter hub 18 form a catheter member 19.

The catheter hub 18 is exposed on the patient's skin in a state where the catheter 16 has been inserted into a blood vessel, and indwelled together with the catheter 16 by being pasted with a tape or the like.

A constituent material of the catheter hub 18 is not particularly limited, but a thermoplastic resin material, such as polypropylene, polycarbonate, polyamide, polysulfone, polyarylate, a methacrylate-butylene-styrene copolymer, or the like may be preferably applied.

A hollow portion 18a that communicates with a lumen 17 (see FIG. 2) of the catheter 16 and through which an infusion solution can flow is provided inside the catheter hub 18. A hemostatic valve, a plug, or the like (not illustrated) may be housed inside the hollow portion 18a in order to inhibit back-flow of blood at the time of puncture with the inner needle 20 and to allow infusion along with insertion of a connector of an infusion tube.

An annular protrusion 28, which protrudes radially outward and revolves in a circumferential direction of the catheter hub 18, is formed near a distal end of an outer peripheral surface of the catheter hub 18. A screw portion 30, which protrudes radially outward in a flange shape and extends in the circumferential direction is provided at an outer peripheral portion of a proximal end of the catheter hub 18, and the connector of the infusion tube (not illustrated) is connected to the screw portion 30 after removal of the inner needle 20. An inner peripheral surface of the proximal end of the catheter hub 18 is formed in a tapered shape that decreases in diameter in a distal end direction.

The inner needle 20 has a longer overall length than the catheter 16 and is inserted through the lumen 17 of the catheter 16 and the hollow portion 18a of the catheter hub 18. A lumen 21 axially penetrating through the inner needle 20 is provided inside the inner needle 20. This lumen communicates with a distal end opening of the inner needle 20. A sharp needle tip 20a is provided at the distal end of the inner needle 20.

In the catheter unit 12 in an initial state, the distal end of the inner needle 20 protrudes from a distal end opening of the catheter 16, and the needle tip 20a is exposed on the distal end side of the catheter 16. Incidentally, a groove portion for confirmation of flashback may be provided along the axial direction on an outer peripheral surface of the inner needle 20. A part of the inner needle 20 may be cut out along the axial direction.

The inner needle 20 has rigidity to be capable of puncturing the skin of the living body. Examples of a constituent material of the inner needle 20 include a metal material such as stainless steel, aluminum or an aluminum alloy, and titanium or a titanium alloy, a hard resin, ceramics, and the like. The inner needle 20 is firmly fixed to the needle hub 22 by an appropriate fixing method (fusion, adhesion, insert molding, and the like).

As illustrated in FIG. 2, the needle hub 22 has a lower wall 32, left and right sidewalls 34a and 34b protruding upward from side edges of the lower wall 32, and a needle holding portion 36 protruding upward from an upper surface of the lower wall 32 and fixedly supporting the proximal end portion of the inner needle 20. In the present embodiment, the upper portion of the needle hub 22 is open.

A housing space 40, configured to house a part of a multiple tube formed of the inner needle 20 and the catheter 16, the catheter hub 18, and the needle protection member 26, is formed inside a three-dimensional structure constituted by the lower wall 32 and the left and right sidewalls 34a and 34b.

The left and right sidewalls 34a and 34b extend in parallel in a longitudinal direction. Each distal-end-side region 41 of the left and right sidewalls 34a and 34b has an upper edge at a relatively high position and each proximal-end-side region 42 forming the proximal end side of the distal-end-side region 41 has an upper edge at a relatively low position. A groove-shaped rail portion 43 extending in the axial direction is provided on an inner surface of the distal-end-side region 41 of each of the sidewalls 34a and 34b. The rail portion 43 houses left and right edge portions of the catheter operation member 24 and guides axial movement of the catheter operation member 24. An arrangement concave portion 66, configured to attach the support member 64, is provided on one of the sidewalls 34a.

Figure 4:
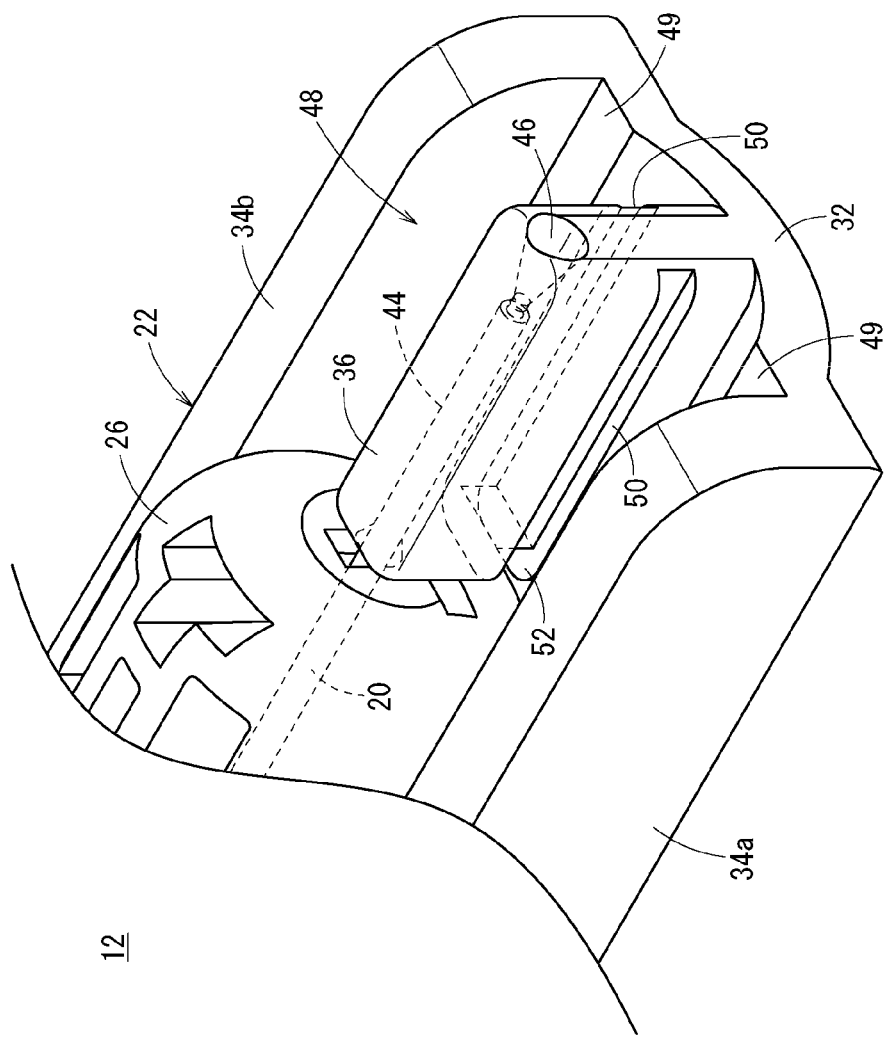
FIG. 4 is a perspective view of the needle hub as viewed from a proximal end side.

As illustrated in FIG. 4, the needle holding portion 36 has a holding hole 44 to hold the proximal end portion of the inner needle 20 and a wire introduction hole 46 formed on the proximal end side of the holding hole 44 and communicating with the lumen 21 of the inner needle 20. The wire introduction hole 46 is formed in a tapered shape that decreases in diameter in the distal end direction.

The wire introduction hole 46 is not necessarily formed in such a tapered shape, and may be, for example, a straight-shaped hole having a constant diameter in the axial direction. In addition, the proximal end of the inner needle 20 may be exposed to the outside of the needle holding portion 36 without providing the wire introduction hole 46. In this case, a guide member 82 may be configured such that a guide wire 80 is properly induced toward the lumen 21 of the inner needle 20.

A first fitting portion 48 having a plurality of female fitting portions 49 open in a proximal end direction is provided at the proximal end portion of the needle hub 22. The first fitting portion 48 receives a part (a second fitting portion 90) of the guide member 82, which will be described later, of the guide wire unit 14, thereby enabling attachment of the guide wire unit 14 to the catheter unit 12. In the present embodiment, the first fitting portion 48 has the left and right (two) female fitting portions 49 provided on the left and right sides of the needle holding portion 36 as the plurality of female fitting portions 49. That is, a groove shape, formed by the lower wall 32, the left and right sidewalls 34a and 34b, and the needle holding portion 36, forms the left and right female fitting portions 49.

In order to suppress the shaking of the guide member 82 in the vertical direction with respect to the needle hub 22 in a state where the guide member 82 is attached to the needle hub 22, concave portions 50 extending in the axial direction are provided on left and right side surfaces of the needle holding portion 36. Each of the concave portions 50 is open on a proximal end surface of the needle holding portion 36. In addition, a notch portion 52 connected to a distal end of each of the concave portions 50 is provided on a distal end surface of the needle holding portion 36 in order to inhibit rearward withdrawal of the guide member 82 from the needle hub 22 in the state where the guide member 82 is attached to the needle hub 22.

A material forming the needle hub 22 is not particularly limited as long as a material that can secure adequate rigidity. For example, the materials exemplified for the catheter hub 18 can be appropriately selected. Incidentally, an external shape of the needle hub 22 is formed in a box shape, which is a combination of substantially flat surfaces, in the present embodiment, but may be formed in a rounded shape in modifications.

As illustrated in FIG. 1, each upper portion of the catheter hub 18 and the needle protection member 26 is exposed from the needle hub 22 in the catheter unit 12. Incidentally, the catheter unit 12 may be configured to cover the catheter hub 18, the needle protection member 26, and the like by forming an upper wall on the needle hub 22 or attaching a lid portion.

The catheter operation member 24 is attached to the catheter hub 18. It is possible to cause the catheter 16 and the catheter hub 18 to advance and retract with respect to the inner needle 20 and the needle hub 22 by operating the catheter operation member 24 in the axial direction. In FIG. 2, the catheter operation member 24 includes an operation plate portion 54 extending in the axial direction and a hub attachment portion 56 that is integrally formed at a proximal end of the operation plate portion 54 and removably attached to the catheter hub 18.

The operation plate portion 54 is a portion on which a user places a finger to perform forward and backward operations of the catheter 16. In the catheter unit 12 in the initial state, distal end sides of left and right edge portions of the operation plate portion 54 are arranged inside the rail portions 43 provided on the left and right sidewalls 34a and 34b of the needle hub 22, and the other portions of the left and right edge portions are arranged on the upper surfaces of the proximal-end-side regions 42 of the left and right sidewalls 34a and 34b.

The operation plate portion 54 is formed to be thin, and thus, is flexible to be easily bendable in a direction orthogonal to a plane direction of the operation plate portion 54 in a side view. A material forming the catheter operation member 24 is not particularly limited, but, for example, the materials exemplified for the catheter hub 18 can be appropriately selected.

A plurality of ribs 58 protruding upward with a relatively low height is provided on the upper surface of the operation plate portion 54 with a space therebetween in a longitudinal direction of the operation plate portion 54. In addition, tabs 60 and 62 each of which has a higher protrusion height than the rib 58 are provided on a distal end side and a proximal end side on the upper surface of the operation plate portion 54. When operating the catheter operation member 24 in the axial direction, the user can perform the operation by contacting the tab 60 or the tab 62 with the finger.

In the present embodiment, the hub attachment portion 56 holds the catheter hub 18 with a light engaging force and each relative axial movement of the hub attachment portion 56 and the catheter hub 18 is inhibited in a state where the hub attachment portion 56 is attached to the catheter hub 18. Specifically, the hub attachment portion 56 is formed in a box shape that is open in downward and proximal end directions. A groove portion (not illustrated) to accommodate the annular protrusion 28 provided in the catheter hub 18 is formed on an inner surface of the hub attachment portion 56.

The relative movement of the catheter operation member 24 and the catheter hub 18 in the axial direction is inhibited by the engagement between the annular protrusion 28 and the groove portion in the state where the hub attachment portion 56 is attached to the catheter hub 18. In the present embodiment, the hub attachment portion 56 is configured to allow rotation of the catheter hub 18 with respect to the hub attachment portion 56 in the state of being attached to the catheter hub 18.

With the above-described configuration, the coupling between the hub attachment portion 56 and the catheter hub 18 is maintained while the hub attachment portion 56 is present in the housing space 40 of the needle hub 22. On the other hand, when the catheter operation member 24 is pushed out in the distal end direction of the needle hub 22 and then lifted upward by the user's operation, the hub attachment portion 56 is detached from the catheter hub 18. Accordingly, the catheter operation member 24 can be separated from the catheter hub 18.

Incidentally, a shape of the hub attachment portion 56 is detachable from the catheter hub 18 and is not limited to the illustrated shape as long as the shape enables the advancing of the catheter hub 18 by the operation in the distal end direction. The hub attachment portion 56 may be configured to inhibit rotation of the catheter hub 18 in the state of being attached to the catheter hub 18. The catheter operation member 24 is not necessarily provided in the catheter assembly 10A.

As illustrated in FIGS. 1 and 2, the needle hub 22 is provided with a support member 64. The support member 64 is configured to suppress deflection of the catheter 16 and the inner needle 20 by supporting the catheter 16 from the lower side, and is rotatably attached to the arrangement concave portion 66 formed at the distal end portion of the needle hub 22.

When the catheter operation member 24 is moved in the distal end direction with respect to the needle hub 22, the support member 64 is pushed by the hub attachment portion 56 and rotated toward the outside of the sidewall 34a. Thus, the support member 64 does not inhibit the detachment of the catheter hub 18 and the needle protection member 26 from the needle hub 22. Incidentally, the support member 64 is not necessarily provided.

In FIG. 2, the needle protection member 26 includes a main body portion 68 housing a shutter 76, a fitting protrusion 70 protruding in the distal end direction from a distal end of the main body portion 68, a plurality of (two in the illustrated example) arms 72 swingably supported by the main body portion 68, and a circular cylindrical operator 74 provided on a proximal end side of the main body portion 68.

In the initial state, the fitting protrusion 70 is separably fitted, in a tapered manner, to the inner peripheral portion of the proximal end of the catheter hub 18. The coupling mode between the needle protection member 26 and the catheter hub 18 is not limited to the tapered fitting, but may be, for example, straight-fitting, concavo-convex fitting, screw-fitting (screwing), or the like.

Each of the arms 72 is supported by the main body portion 68 with a position on a slightly proximal side of a central portion in the longitudinal direction as a fulcrum. An engagement groove 73 is provided on an inner side of a distal end portion of each of the arms 72, and the flange-shaped screw portion 30 provided in the catheter hub 18 is inserted (fits) into the engagement groove 73 in the initial state.

Although not illustrated in detail, an inner protrusion protruding inward is provided at a proximal end portion of each of the arms 72. In the initial state, an inner end of the inner protrusion approaches or contacts an outer surface of the inner needle 20, whereby inward displacement of the proximal end portion of the arm 72 is inhibited by the inner needle 20. As a result, expansion on the distal end side of the arm 72 is inhibited.

The shutter 76 is arranged inside the needle protection member 26. The shutter 76 in the illustrated example has a form of a leaf spring that is formed by bending a metal plate member. In the initial state, the shutter 76 is compressed by being pressed by the outer surface of the inner needle 20. On the other hand, the shutter 76 is expanded (opened) by an elastic restoring force when the inner needle 20 retracts with respect to the needle protection member 26 and the needle tip 20a of the inner needle 20 moves toward the proximal end side of the shutter 76. Accordingly, a needle insertion path inside the needle protection member 26 is blocked. A retaining member (not illustrated) is arranged inside a proximal end portion of the needle protection member 26 such that the inner needle 20 is not withdrawn from the needle protection member 26 in the proximal end direction.

The needle protection member 26 is made of, for example, a hard resin. The hard resin can be selected from the materials exemplified as the constituent materials of the catheter hub 18.

Figure 3:
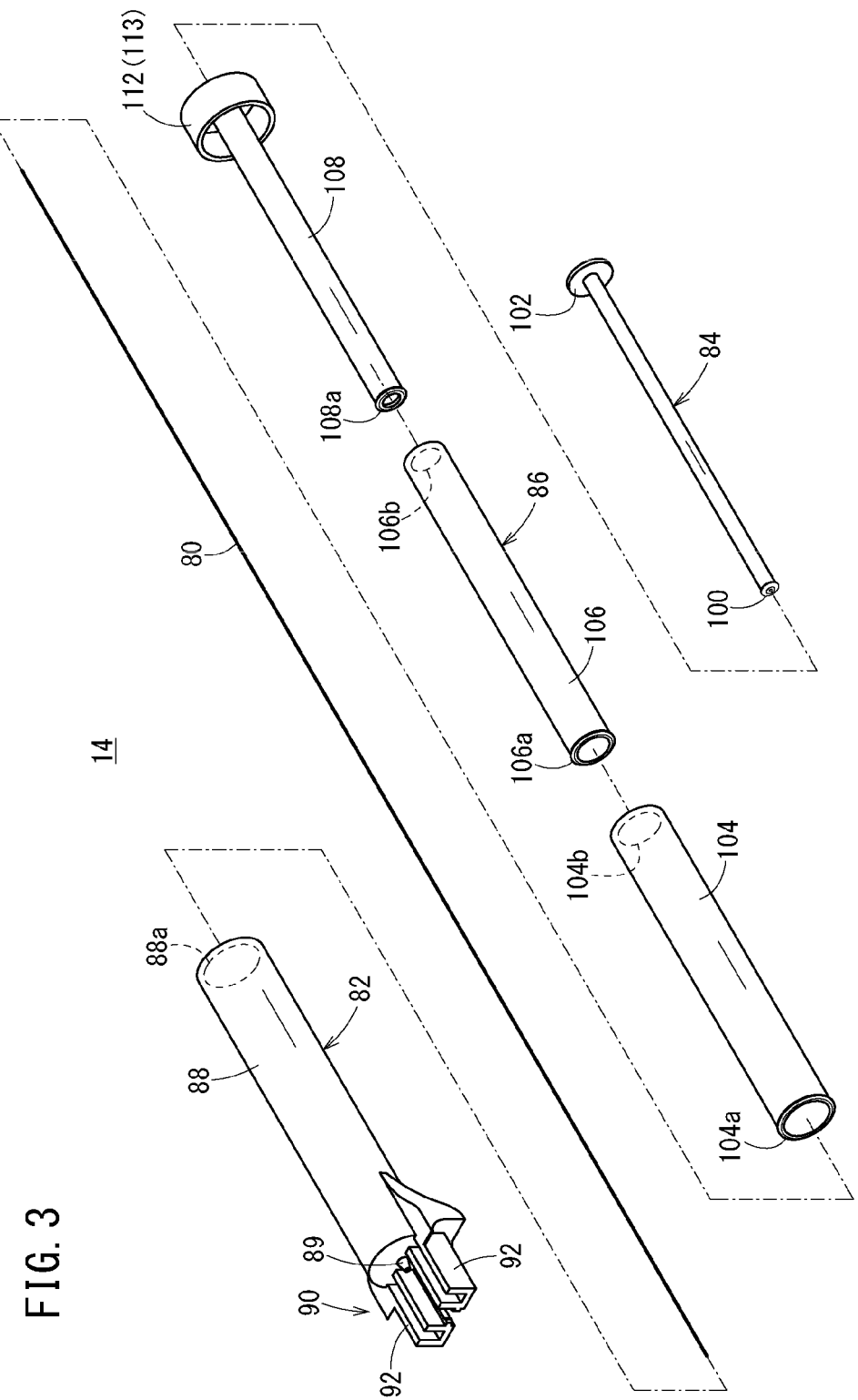
FIG. 3 is an exploded perspective view of a guide wire unit.

The guide wire unit 14 is separated from the catheter unit 12 in the state of the catheter assembly 10A provided as a product. In FIG. 3, the guide wire unit 14 includes the guide wire 80, the guide member 82, which is attachable to the proximal end portion of the needle hub 22 and guides the guide wire 80, a wire operation member 84 fixed to a proximal end portion of the guide wire 80, and a cover 86 that covers the guide wire 80 and is arranged between the guide member 82 and the wire operation member 84.

The guide wire 80 guides the catheter 16 when inserting the catheter 16 into the blood vessel in order to cause the catheter 16 to indwell in the patient. The guide wire 80 is a fine linear member having flexibility, can be inserted into the lumen of the inner needle 20, and is longer than the inner needle 20 and the catheter 16. A constituent material of the guide wire 80 is not particularly limited, and, for example, various metal materials such as stainless steel and a Ni—Ti alloy can be used.

The guide member 82 is configured to guide the guide wire 80 toward the inner needle 20. Specifically, the guide member 82 includes a body portion 88 having a hollow cylindrical shape and a second fitting portion 90 having a plurality of male fitting portions 92 protruding in the distal end direction from the distal end of the body portion 88. In the guide wire unit 14 in the initial state, a distal end region of the guide wire 80 is housed inside the body portion 88.

Figure 5:
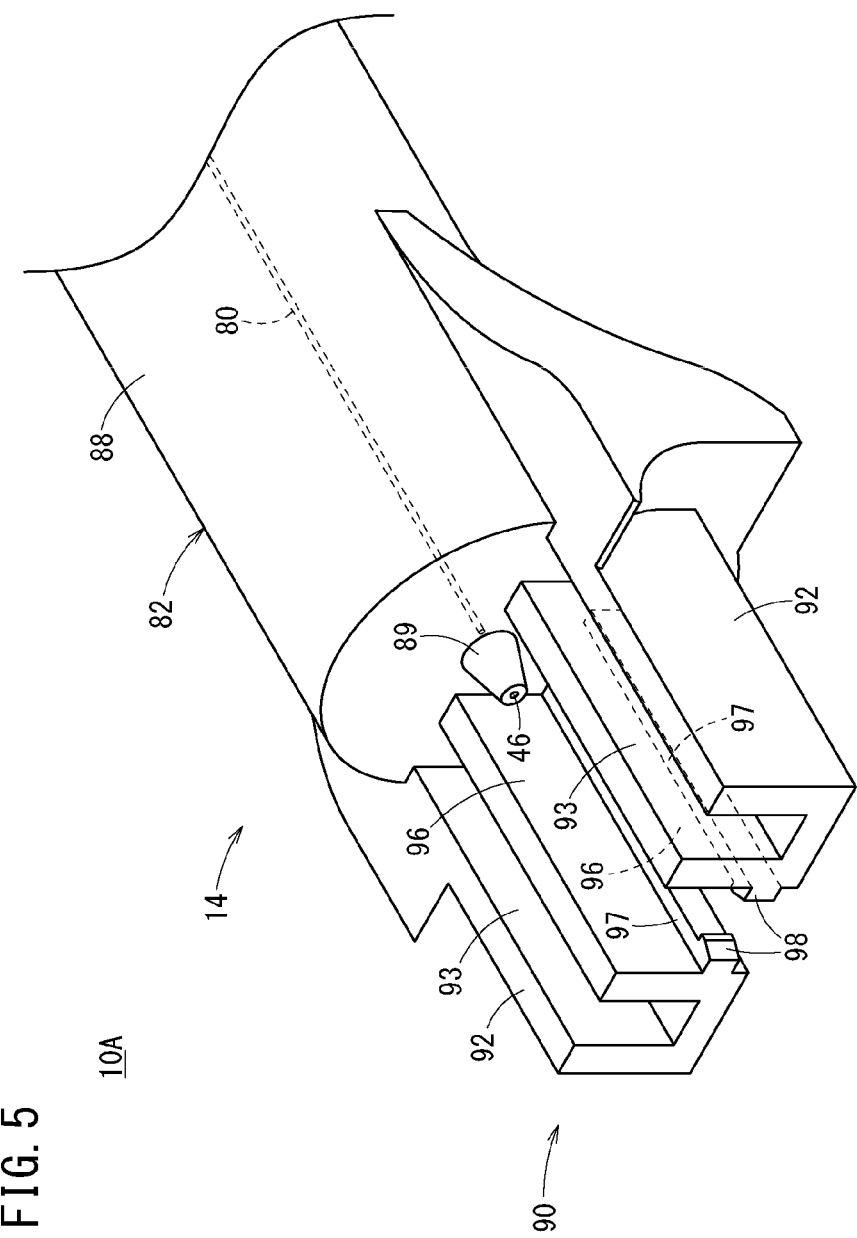
FIG. 5 is a perspective view of a guide member as viewed from a distal end side.

In FIG. 5, the body portion 88 is formed in a hollow circular cylindrical shape, and an insertion protrusion 89 slightly protruding in the distal end direction is provided at a center portion of a distal end of the body portion 88. The insertion protrusion 89 is insertable into the wire introduction hole 46 formed in the needle holding portion 36 of the needle hub 22 and has an outer peripheral surface whose outer diameter decreases in the distal end direction.

Figure 7:
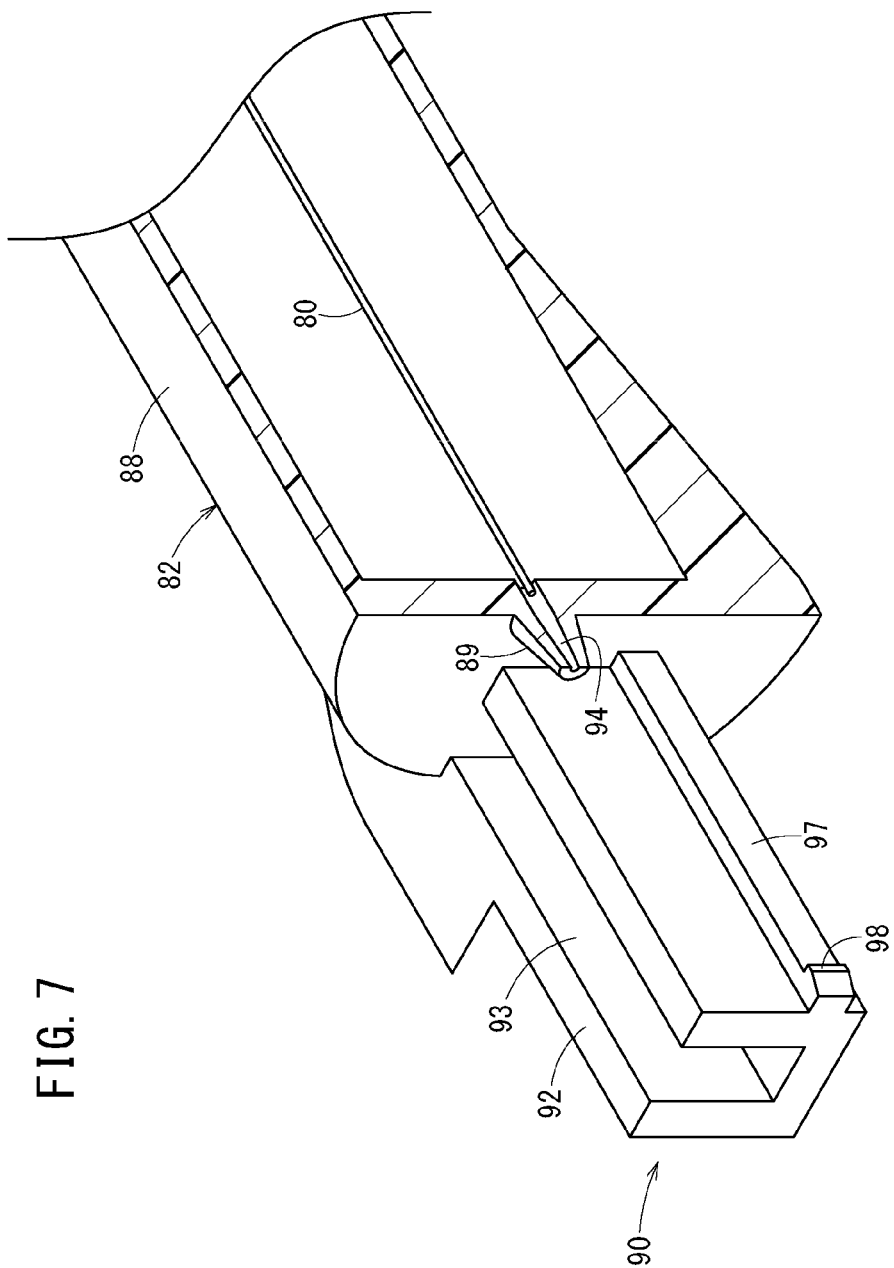
FIG. 7 is a perspective cross-sectional view of the guide member.

In addition, a wire lead-out hole 94 penetrating in the axial direction and communicating with a lumen of the body portion 88 is formed in the insertion protrusion 89 as illustrated in FIG. 7. The wire lead-out hole 94 is coaxial with the lumen 21 of the inner needle 20 in the state where the guide member 82 is attached to the needle hub 22. The wire lead-out hole 94 in the illustrated example has a tapered shape that decreases in diameter in the distal end direction. Incidentally, the wire lead-out hole 94 may have a straight shape having a constant diameter in the axial direction.

In the present embodiment, the distal end of the guide wire 80 is arranged inside the wire lead-out hole 94 in the initial state of the guide wire unit 14. Incidentally, in modifications, the distal end of the guide wire 80 may protrude in the distal end direction from the distal end of the wire lead-out hole 94, and may protrude in the distal end direction from the distal end of the guide member 82 (that is, the distal end of the male fitting portion 92).

In FIG. 3, a proximal opening portion is formed at the proximal end of the body portion 88. In addition, a locking protrusion 88a protruding inward is provided on the inner peripheral portion of the proximal end of the body portion 88.

In FIG. 5, the second fitting portion 90 having the plurality of male fitting portions 92 is a part that can be fitted to the first fitting portion 48 having the plurality of female fitting portions 49 provided at the proximal end portion of the needle hub 22.

In the present embodiment, the guide member 82 is provided with the two left and right male fitting portions 92. The left and right male fitting portions 92 are parallel to each other with a space therebetween on the left and right of the insertion protrusions 89. Each of the male fitting portions 92 is formed with a groove 93 that is open in the distal end direction and upward and extends in the axial direction.

Figure 6:
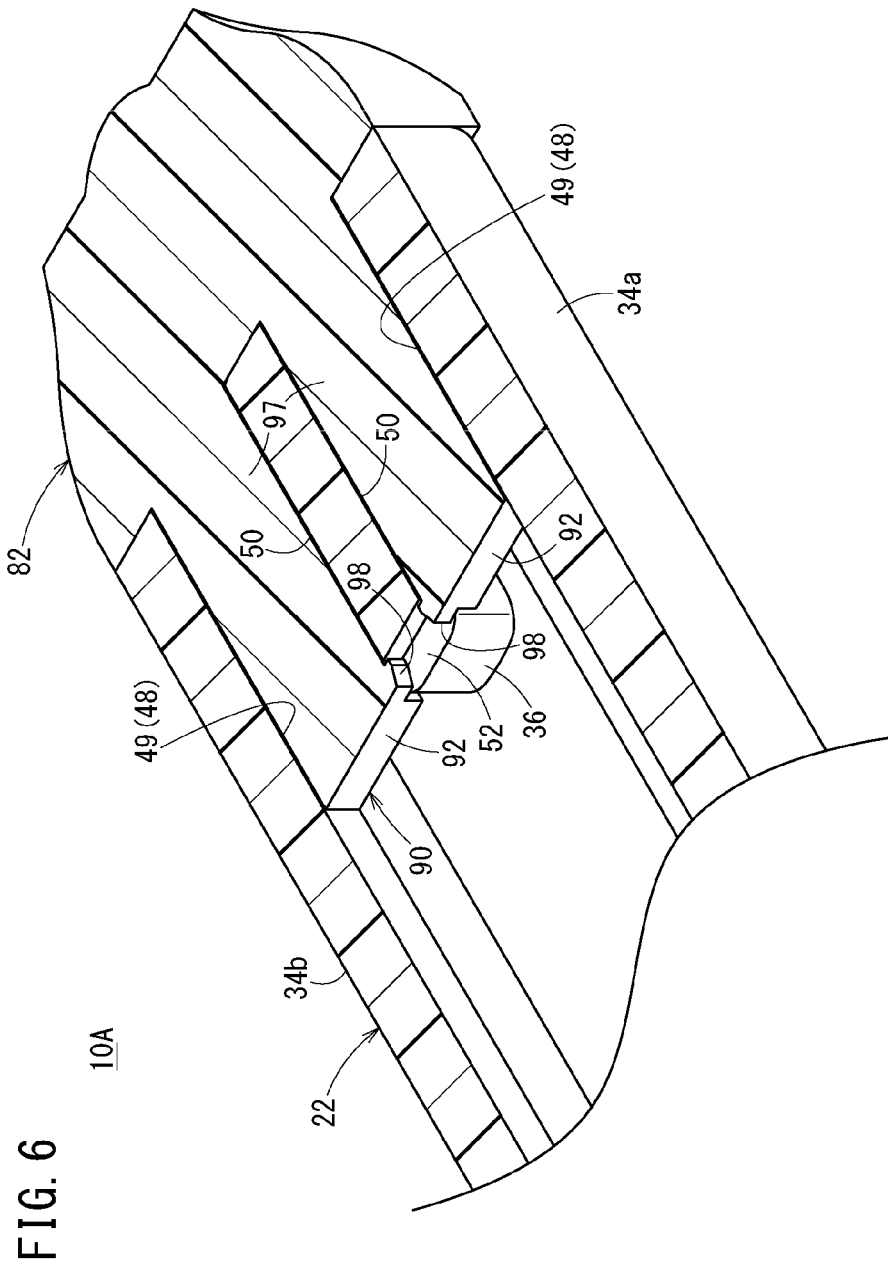
FIG. 6 is a cross-sectional view illustrating a fitting structure between the needle hub and the guide member.

In FIGS. 5 and 6, convex portions 97, which can be fitted to the concave portions 50, respectively, provided in the needle holding portion 36 and extend in the axial direction, are provided on the sidewall surfaces 96 opposing each other of the left and right male fitting portions 92. Engagement protrusions 98 that can be engaged with the distal ends of the concave portion 50 are provided at distal ends of the convex portion 97. Incidentally, FIG. 6 does not illustrate the needle protection member 26.

The convex portions 97 may be provided on outer sidewall surfaces of the left and right male fitting portions 92 instead of being provided on the inner sidewall surfaces 96 of the left and right male fitting portions 92. In this case, the concave portions 50 are provided on inner surfaces of the sidewalls 34a and 34b of the needle hub 22 instead of being provided on the side surfaces of the needle holding portion 36. In addition, the engagement protrusion 98 is not necessarily provided on the convex portion 97, and may be provided at a location other than the convex portion 97 in the male fitting portion 92. In this case, an engaged portion (a groove or the like) with which the convex portion 97 can be engaged is provided in the needle hub 22 in accordance with a position of the convex portion 97 provided in the male fitting portion 92.

In FIG. 1, the wire operation member 84 is an operation portion configured to perform the operation of inserting the guide wire 80 into the blood vessel prior to the operation of inserting the catheter 16 into the blood vessel of the patient. The wire operation member 84 is configured to support the guide wire 80, be capable of performing relative displacement in the axial direction with respect to the guide member 82, and moves the guide wire 80 with respect to the guide member 82 along with the displacement. In the present embodiment, the wire operation member 84 is a narrow round bar-shaped member and is fixed to the proximal end portion of the guide wire 80.

As illustrated in FIG. 3, an annular flange portion 100, which slightly protrudes radially outward and extends in the circumferential direction, is provided at a distal end of the wire operation member 84 in order to inhibit the wire operation member 84 from being withdrawn from the cover 86 in the proximal end direction. In addition, a finger contact portion 102 protruding radially outward and extending in the circumferential direction is provided at a proximal end of the wire operation member 84 such that the user easily operates the wire operation member 84 in the axial direction.

The cover 86 is formed in a hollow cylindrical shape so as to cover the guide wire 80 between the guide member 82 and the wire operation member 84 in the initial state, and is configured to axially contract as the wire operation member 84 moves in the distal end direction with respect to the guide member 82. In the present embodiment, the cover 86 has a telescopic structure in which a plurality of tubular members having different sizes is combined so as to be relatively movable in the axial direction. Specifically, the cover 86 has three tubular members (first to third tubular members 104, 106, and 108) that are axially slidable and have different outer diameters.

The first tubular member 104 is formed to have a smaller diameter than the body portion 88 of the guide member 82 and is inserted inside the body portion 88 so as to be axially slidable. In FIG. 3, an annular flange portion 104a protruding radially outward is provided on an outer peripheral portion of a distal end of the first tubular member 104. The annular flange portion 104a is locked by the locking protrusion 88a provided on the inner peripheral portion of the proximal end of the body portion 88 so that the withdrawal of the first tubular member 104 from the body portion 88 in the proximal end direction (rearward withdrawal) is inhibited. An annular locking protrusion 104b protruding radially inward is provided on an inner peripheral portion of a proximal end of the first tubular member 104.

The second tubular member 106 is formed to have a smaller diameter than the first tubular member 104 and is inserted inside the first tubular member 104 so as to be axially slidable. An annular flange portion 106a protruding radially outward is provided on an outer peripheral portion of a distal end of the second tubular member 106. The annular flange portion 106a is locked by the locking protrusion 104b provided on the inner peripheral portion of the proximal end of the first tubular member 104 so that the withdrawal of the second tubular member 106 from the first tubular member 104 in the proximal end direction (rearward withdrawal) is inhibited. An annular locking protrusion 106b protruding radially inward is provided on an inner peripheral portion of a proximal end of the second tubular member 106.

The third tubular member 108 is formed to have a smaller diameter than the second tubular member 106 and is inserted inside the second tubular member 106 so as to be axially slidable. An annular flange portion 108a protruding radially outward is provided on an outer peripheral portion of a distal end of the third tubular member 108. The annular flange portion 108a is locked by the locking protrusion 106b provided on the inner peripheral portion of the proximal end of the second tubular member 106 so that the withdrawal of the third tubular member 108 from the second tubular member 106 in the proximal end direction (rearward withdrawal) is inhibited.

Figure 8:
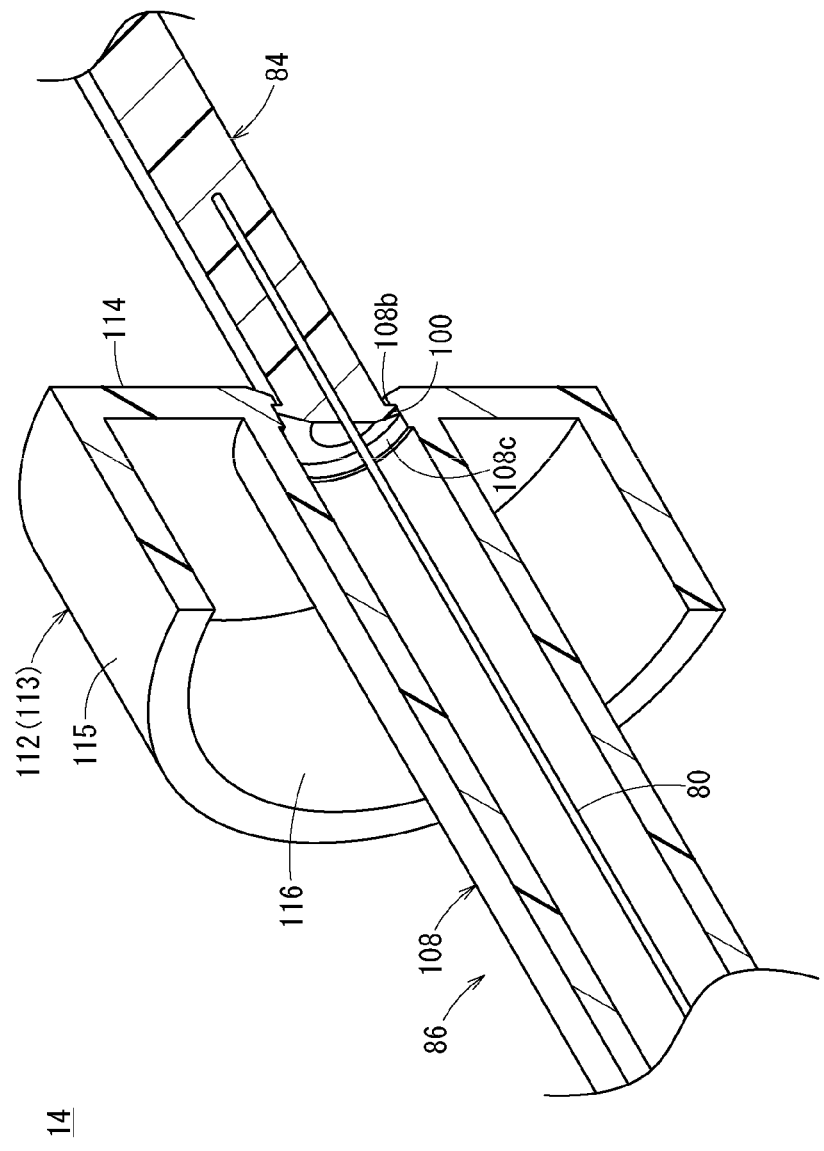
FIG. 8 is a perspective cross-sectional view of a third tubular member and a wire operation member.

In FIG. 8, an annular locking protrusion 108b protruding radially inward is provided on an inner peripheral portion of a proximal end of the third tubular member 108. The annular flange portion 100 provided at the distal end of the wire operation member 84 is locked by the locking protrusion 108b so that the withdrawal of the wire operation member 84 from the third tubular member 108 in the proximal end direction (rearward withdrawal) is inhibited.

A fitting portion 108c, which is adjacent to the distal end side of the locking protrusion 108b and fitted with the annular flange portion 100 of the wire operation member 84 in the initial state, is provided in the inner peripheral portion of the proximal end of the third tubular member 108. An inner diameter of the fitting portion 108c is slightly smaller than an inner diameter of a portion of a lumen of the third tubular member 108, the portion on the distal end side of the fitting portion 108c The annular flange portion 100 of the wire operation member 84 is fitted to the fitting portion 108c with a relatively small fitting force that causes detachment from the fitting portion 108c in the distal end direction when the user operates the wire operation member 84 in the distal end direction. Accordingly, the wire operation member 84 is releasably fixed to the cover 86 at a position on the most proximal end side within a movable range with respect to the cover 86.

In addition, the cover 86 is provided with a lock mechanism 112 that holds a contracted state of the cover 86 when the cover 86 is in a state of contracting in the axial direction to the maximum extent (contracted state). In the present embodiment, a lock tube 113 provided on the outer peripheral portion of the proximal end of the third tubular member 108 functions as the above-described lock mechanism 112. Specifically, the lock tube 113 includes a radial wall 114 extending radially outward from the proximal end of the third tubular member 108, and an axial wall 115 extending from an outer end of the radial wall 114 in the distal end direction. An annular concave portion 116 open in the distal end direction is formed between the axial wall 115 and an outer peripheral surface of the third tubular member 108.

The lock tube 113 can be fitted to the outer peripheral portion of the proximal end of the body portion 88 of the guide member 82 from the outside. In a state (see FIG. 10) where the lock tube 113 and the body portion 88 are fitted to each other, the third tubular member 108 and the guide member 82 are fixed to each other due to a frictional resistance caused by contact between the inner peripheral surface of the lock tube 113 and the outer peripheral surface of the body portion 88. Accordingly, the cover 86 is suppressed from stretching again after the cover 86 is turned into the contracted state.

Incidentally, a fixing force, applied on each other between the guide member 82 and the third tubular member 108, generated by the lock tube 113 is not required to be a strong fixing force, but may be a fixing force to an extent that can suppress unintentional stretching of the contracted cover 86. For example, a claw that can be engaged with the outer peripheral surface of the third tubular member 108 may be provided in the lock tube 113 so as to firmly fix the guide member 82 and the third tubular member 108 by the engagement of the claw.

The configuration of the lock mechanism 112 is not limited to the above-described lock tube 113. For example, in a modification of the lock mechanism 112, it may be configured such that relative displacement in the axial direction between members radially adjacent to each other among the guide member 82 and the first to third tubular members 104, 106, and 108 is inhibited or suppressed in the contracted state of the cover 86 by engagement or fitting.

A material forming the cover 86 is not particularly limited as long as being adequately hard. For example, the materials exemplified for the catheter hub 18 can be appropriately selected.

The cover 86 may be configured of two or less tubular members, or may be configured of four or more tubular members. In either case, the lock tube 113 is provided in the innermost cylindrical member. In order to inhibit the cover 86 from unintentionally shrinking, a mechanism that temporarily fixes the cover 86 to a length in the initial state (see FIG. 1) may be provided on the cover 86. Such a mechanism for the temporary fixing can be implemented, for example, by fitting or engagement between tubular members adjacent to each other.

Next, functions and effects of the catheter assembly 10A configured as described above will be described. The catheter assembly 10A can be used, for example, according to the following procedure.

(1) Guide Wire Necessity Determination

At the time of treatment using the catheter assembly 10A, the user determines whether to use the guide wire 80. Specifically, whether to use the guide wire 80 is determined based on blood vessel information (depth, narrowness, presence or absence of stenosis, and the like of the blood vessel) obtained by ultrasound guide, experience of failing to secure the blood vessel of the patient, and the like.

(2) Attachment of Guide Wire Unit

Figure 9:
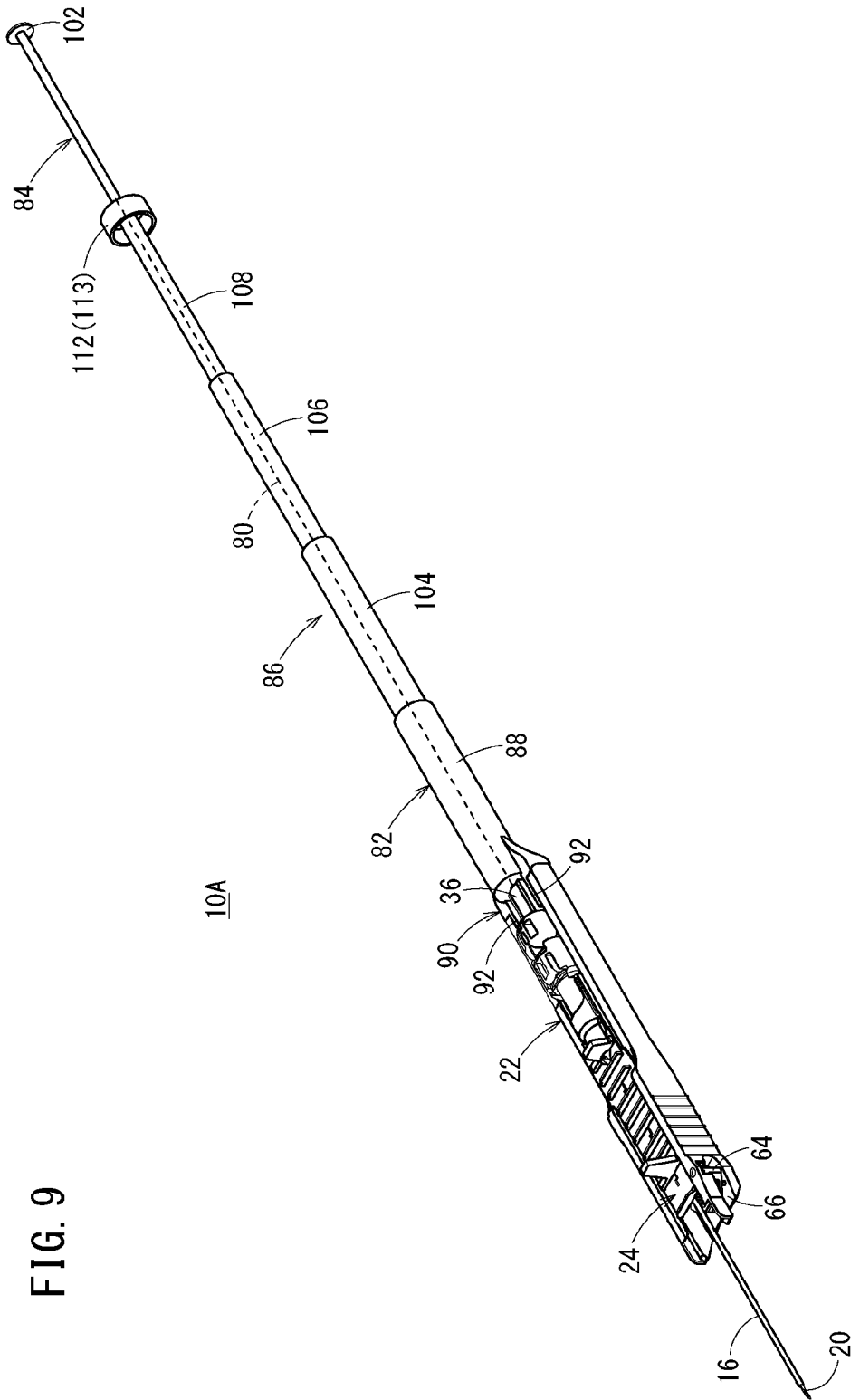
FIG. 9 is a first view for describing a method of using the catheter assembly illustrated in FIG. 1.

When it is determined that the use of the guide wire 80 is necessary, the user attaches the guide wire unit 14 in the initial state to the catheter unit 12 in the initial state as illustrated in FIG. 9. Specifically, the second fitting portion 90 (the plurality of male fitting portions 92) provided in the guide member 82 is fitted to the first fitting portion 48 (the plurality of female fitting portions 49) (see FIG. 2 and the like) provided at the proximal end portion of the needle hub 22 through a proximal end opening of the female fitting portion 49.

When the second fitting portion 90 is fitted to the first fitting portion 48, the convex portion 97 (see FIG. 5) enters the concave portion 50 (see FIG. 4). In a state (hereinafter also referred to as a "attached state") where the attachment of the guide member 82 onto the needle hub 22 is completed as the male fitting portion 92 is completely fitted to the female fitting portion 49, the convex portion 97 and the concave portion 50 are fitted to each other over a certain range in the axial direction as illustrated in FIG. 6. Thus, the shaking of the guide member 82 in the vertical direction with respect to the needle hub 22 is suppressed.

In addition, as the male fitting portion 92 enters the female fitting portion 49, the engagement protrusion 98 advances in the distal end direction inside the concave portion 50, and is caught by the notch portion 52 at the time of reaching the notch portion 52 continuous to the distal end of the concave portion 50. Accordingly, the engagement protrusion 98 is engaged with the needle holding portion 36 in the attached state. With this engagement, the guide member 82 is inhibited from being withdrawn from the needle hub 22 in the proximal end direction.

(3) Position Setting of Guide Wire Distal End

Figure 10:
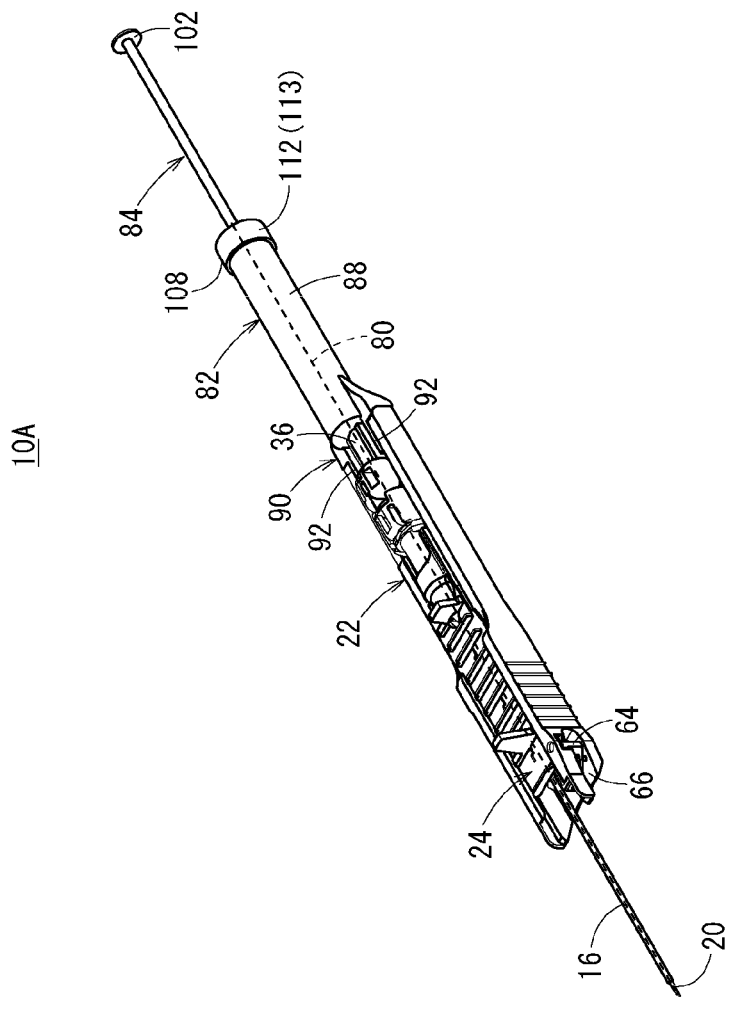
FIG. 10 is a second view for describing the method of using the catheter assembly illustrated in FIG. 1.

Next, as the user operates the guide wire unit 14, the guide wire 80 is introduced into the lumen 21 of the inner needle 20 as illustrated in FIG. 10, and the distal end of the guide wire 80 is arranged in the lumen 21 (the zero protrusion length position) of the distal end portion of the inner needle 20. Incidentally, at the zero protrusion length position, the distal end (the most distal end position) of the guide wire 80 is at the same position as the distal end of the inner needle 20 or on slightly closer to the proximal end side (for example, near the notch provided in the inner needle 20) than the distal end of the inner needle 20. Therefore, the guide wire 80 does not protrude from the distal end of the inner needle 20.

Specifically, the cover 86 is contracted in the axial direction. At this time, the wire operation member 84 inhibited from being withdrawn rearward from the third tubular member 108 is also moved in the distal end direction along with the relative displacement of the proximal end portion (the third tubular member 108) of the cover 86 in the distal end direction with respect to the guide member 82. In addition, the guide wire 80 having the proximal end portion fixed to the wire operation member 84 is moved in the distal end direction along with the movement of the wire operation member 84. At that time, the distal end of the guide wire 80 moves from the wire lead-out hole 94 (see FIG. 7) to the lumen 21 of the inner needle 20 through the wire introduction hole 46 (see FIG. 5), and advances in the distal end direction in the lumen 21 of the inner needle 20.

Then, the distal end of the guide wire 80 is positioned at the lumen 21 of the distal end portion of the inner needle 20 (the zero protrusion length position) in a state where the cover 86 contracts in the axial direction to the maximum extent. At this time, the wire operation member 84 is releasably fixed to the cover 86 at a position on the most proximal end side within the movable range with respect to the cover 86 under the fitting action between the fitting portion 108c and the annular flange portion 100 (see FIG. 8). Therefore, it is possible to inhibit the guide wire 80 from protruding from the distal end of the inner needle 20 before puncturing the patient.

In addition, the stretching of the cover 86 is suppressed by the lock mechanism 112 (the lock tube 113) in the state where the cover 86 contracts in the axial direction to the maximum extent. Therefore, it is possible to inhibit the guide wire 80 from retracting after the distal end of the guide wire 80 has been arranged at the zero protrusion length position.

(4) Puncturing Operation

Next, the user performs a puncturing operation to puncture the skin of the patient with the catheter unit 12. In the puncturing operation, the user presses the distal end portion (the distal end portion of the catheter 16 through which the inner needle 20 is inserted) of the catheter unit 12 against the patient while gripping the needle hub 22, thereby puncturing the skin with the catheter unit 12 toward the puncture target blood vessel. Accordingly, the skin is punctured with the inner needle 20 and the distal end portion of the catheter 16.

(5) Guide Wire Advancing Operation

Figure 11:
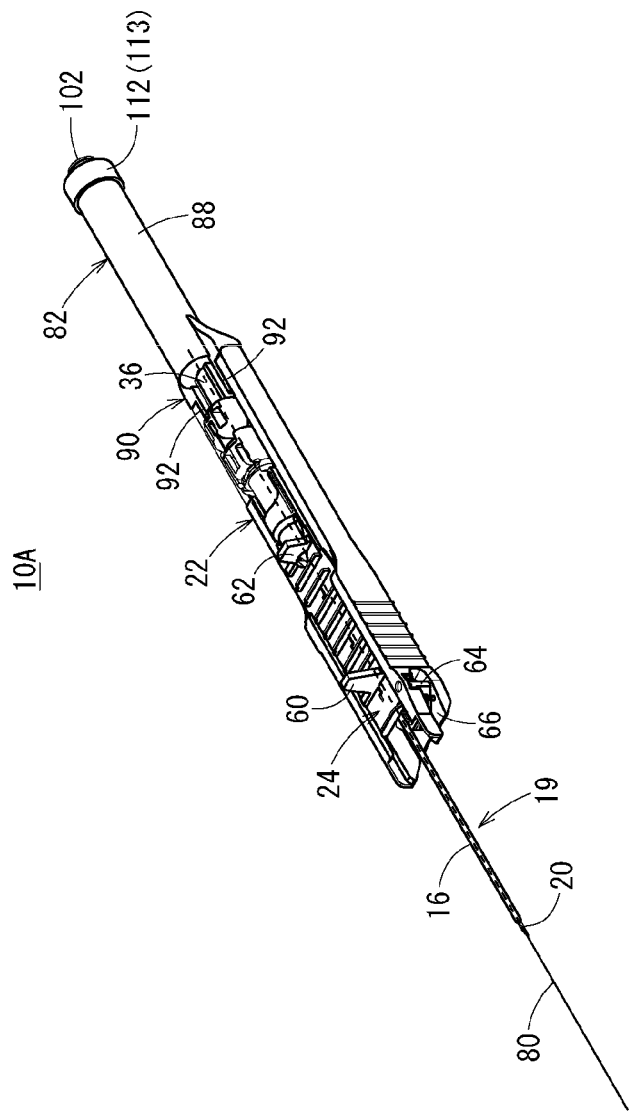
FIG. 11 is a third view for describing the method of using the catheter assembly illustrated in FIG. 1.

Next, the user moves the wire operation member 84 in the distal end direction with respect to the guide member 82 while holding the position of the needle hub 22 in the state where the skin is punctured with the inner needle 20 and the distal end of the catheter 16 as illustrated in FIG. 11. Accordingly, the guide wire 80 is caused to protrude from the distal end opening of the inner needle 20 by a predetermined length. As a result, the distal end portion of the guide wire 80 is inserted into a target position in the blood vessel.

(6) Catheter Advancing Operation

Next, the user operates the catheter operation member 24 in the distal end direction to cause the catheter member 19 (the catheter 16 and the catheter hub 18) to advance while fixing the position of the needle hub 22. In this case, for example, the user contacts the tab 60 or the tab 62 of the catheter operation member 24 with the finger to cause the catheter operation member 24 to slide in the distal end direction relative to the needle hub 22. Accordingly, the catheter 16 is inserted to the target position in the blood vessel. Incidentally, the catheter operation member 24 is moved forward while bending the operation plate portion 54 of the catheter operation member 24 upward in order to inhibit the catheter operation member 24 from coming into contact with the patient's skin.

(7) Inner Needle Removal Operation

Figure 12:
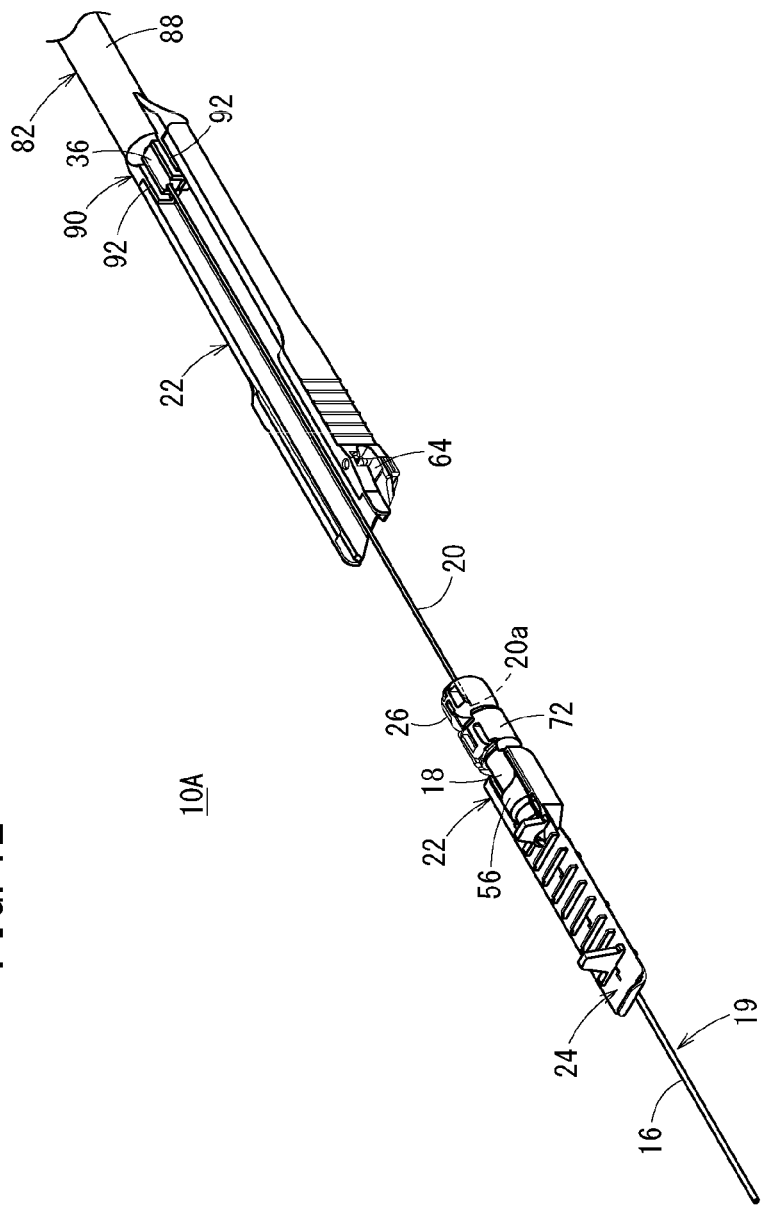
FIG. 12 is a fourth view for describing the method of using the catheter assembly illustrated in FIG. 1.

Next, the user pulls the needle hub 22 in the proximal end direction while holding the positions of the catheter operation member 24 and the catheter member 19. Accordingly, the catheter member 19 and the catheter operation member 24 completely come out of the needle hub 22, and the inner needle 20 having fixed to the needle hub 22 is removed from the catheter 16 as illustrated in FIG. 12.

At this time, in the present embodiment, a safety function is provided by the needle protection member 26 and the shutter 76 (see FIG. 2). That is, the shutter 76 blocks the needle insertion path inside the needle protection member 26 as the needle tip 20a moves to the proximal end side of the shutter 76 inside the needle protection member 26. Accordingly, the inner needle 20 is inhibited from protruding again from the distal end of the needle protection member 26.

In addition, when the needle tip 20a moves to the proximal end side of the inner protrusion provided at the proximal end of the arm 72 inside the needle protection member 26, the inhibition of the inward displacement of the inner protrusion by the inner needle 20 is released, thereby forming a state where the distal end side of the arm 72 can be expanded. Thus, when the needle hub 22 is further pulled in the proximal end direction from the state of FIG. 12, the connection between the catheter hub 18 and the needle protection member 26 is released. Accordingly, the needle protection member 26 is separated from the catheter hub 18 as illustrated in FIG. 13.

(8) Detachment of Catheter Operation Member

Figure 13:
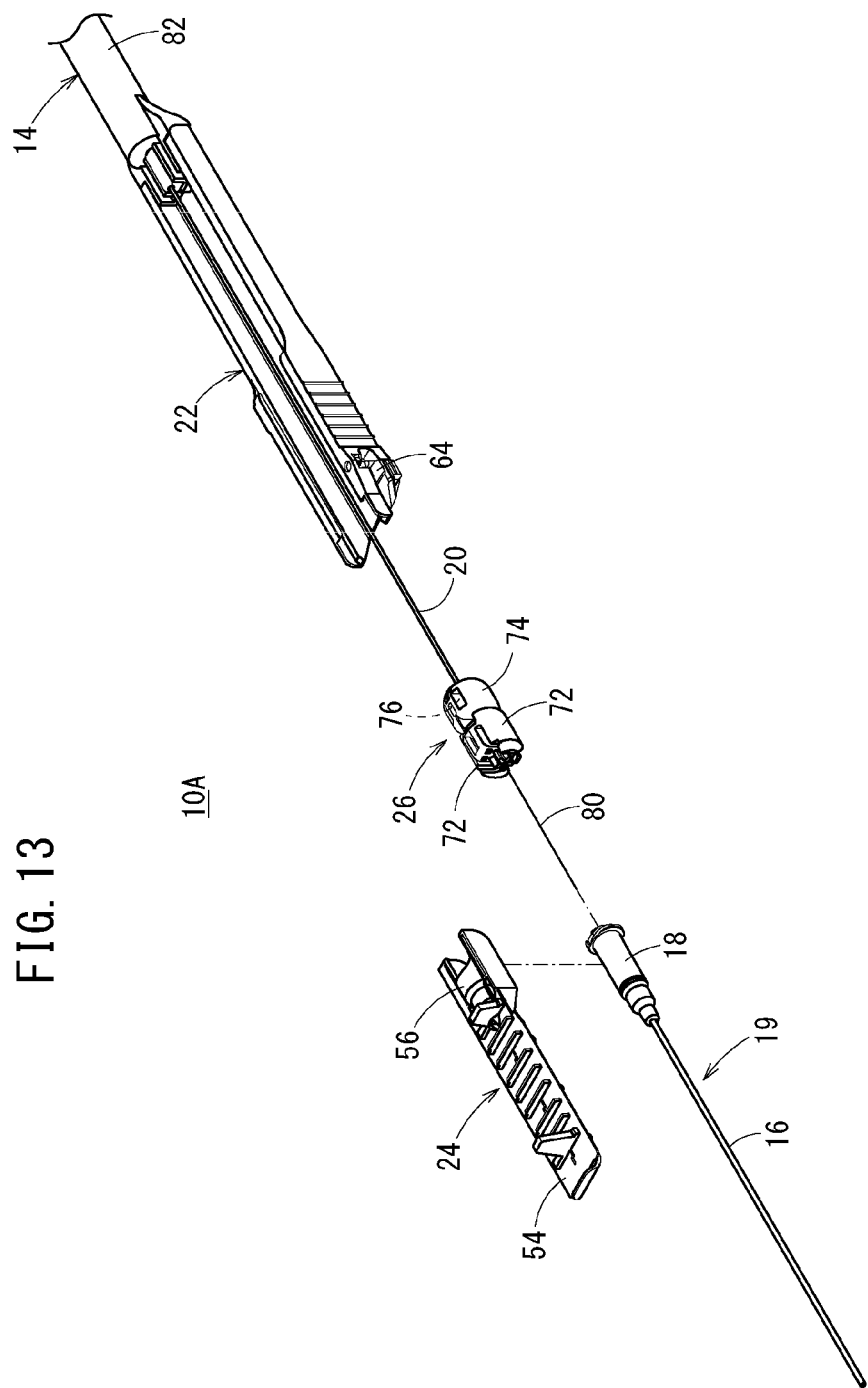
FIG. 13 is a fifth view for describing the method of using the catheter assembly illustrated in FIG. 1.

Next, the user detaches the catheter operation member 24 from the catheter hub 18 as illustrated in FIG. 13. Accordingly, the catheter member 19 is indwelled in the patient. Incidentally, the catheter operation member 24 may be kept attached to the catheter hub 18 depending on a preference of the user.

(9) Administration of Infusion Solution

Next, the connector of the infusion tube (not illustrated) is connected to the proximal end side (the proximal end portion of the catheter hub 18) of the catheter member 19 from which the inner needle 20 has been removed, and the infusion solution (medicinal liquid) is administered from the infusion tube to the patient.

Meanwhile, when it is determined that the use of the guide wire 80 is unnecessary in the guide wire necessity determination in the above-described (1), the same operation as the case of using the guide wire 80 is performed without the above-described (2), (3) and (5), whereby the catheter 16 is indwelled inside the patient's body. Incidentally, there may be a case where it is considered to use the guide wire 80 after starting the puncture even when it is determined that the use of the guide wire 80 is unnecessary at the above-described stage of (1). In such a case, the above-described (2), (3) and (5) may be performed subsequently to the above-described (4) or (6).

As described above, according to the catheter assembly 10A, the guide wire unit 14 is not used when the catheter 16 is indwelled in a patient for which the catheter is likely to be simply indwelled, and thus, the operation thereof is simple, the operation is easy to learn, and the device is also compact. In addition, when the catheter 16 is indwelled in a patient for which the catheter is likely to be hardly indwelled, it is possible to perform smooth indwelling by attaching the guide member 82 to the needle hub 22 and using the guide wire 80. In this manner, it is possible to enjoy advantages of both the cases by selecting whether to use the guide wire 80 depending on a situation.

In addition, the catheter assembly 10A according to the present embodiment includes the wire operation member 84, which is relatively displaceable in the axial direction with respect to the guide member 82, and the guide wire 80 moves forward along with the operation of the wire operation member 84 in the axial direction. With this configuration, it is possible to insert the guide wire 80 into the blood vessel with a simple operation.

Further, the catheter assembly 10A according to the present embodiment includes the cover 86 that contracts in the axial direction along with the movement of the wire operation member 84 in the distal end direction with respect to the guide member 82, and thus, the guide wire 80 is covered by the cover 86 in the initial state. Accordingly, it is possible to inhibit contamination of the guide wire 80.

In the present embodiment, the distal end of the guide wire 80 is positioned in the lumen 21 of the distal end portion of the inner needle 20 in a state where the guide member 82 is attached to the needle hub 22, the cover 86 contracts in the axial direction to the maximum extent, and the wire operation member 84 is positioned on the most proximal end side with respect to the cover 86. With this configuration, it is possible to easily arrange the distal end of the guide wire 80 at the zero protrusion length position. Therefore, it is possible to puncture the patient with the catheter assembly 10A in the state of the zero protrusion length position, and to efficiently insert the guide wire 80 into the blood vessel thereafter.

In particular, since the wire operation member 84 is releasably fixed to the cover 86 at a position on the most proximal end side within the movable range with respect to the cover 86, it is possible to temporarily fix the distal end of the guide wire 80 to the zero protrusion length position and to inhibit the guide wire 80 from protruding from the distal end of the inner needle 20 before puncturing the patient. Moreover, since the cover 86 is provided with the lock mechanism 112 fixing the cover 86 to the guide member 82 when the cover 86 contracts in the axial direction to the maximum extent, it is possible to inhibit the guide wire 80 from retracting after the distal end of the guide wire 80 is arranged at the zero protrusion length position.

In the present embodiment, the cover 86 has the telescopic structure in which the plurality of tubular members 104, 106, and 108 having different sizes is combined so as to be relatively movable in the axial direction. With this configuration, it is possible to move the wire operation member 84 smoothly in the distal end direction with respect to the guide member 82.

Figure 14:
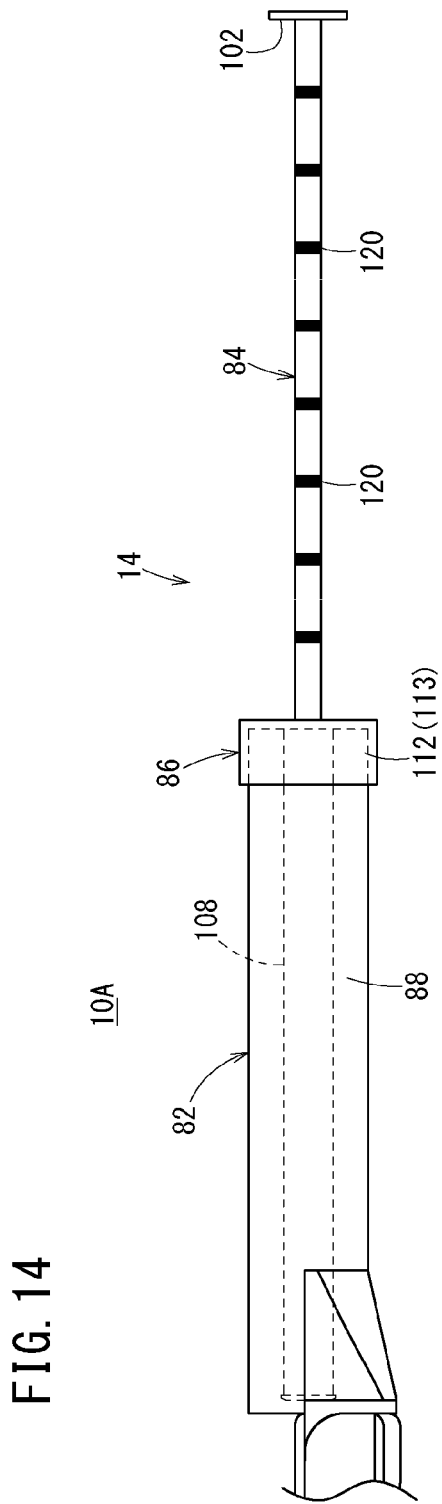
FIG. 14 is a side view of a guide wire unit according to a first modification.

The guide wire unit 14 may be provided with a mechanism configured to indicate a protrusion length of the guide wire 80 from the distal end of the inner needle 20. Such a mechanism may have a form of a plurality of markers 120, provided with a space therebetween in the axial direction on the surface of the wire operation member 84, for example, as illustrated in FIG. 14. The plurality of markers 120 function as scales. When the user operates the wire operation member 84 in the distal end direction in the state where the cover 86 contracts in the axial direction to the maximum extent, it is possible to know the protrusion length of the guide wire 80 from the distal end of the inner needle 20 by viewing the marker 120 while referring to a proximal end surface (a proximal end surface of the third tubular member 108) of the cover 86 as a reference position. Numerals may be added to these markers 120.

Figure 15:
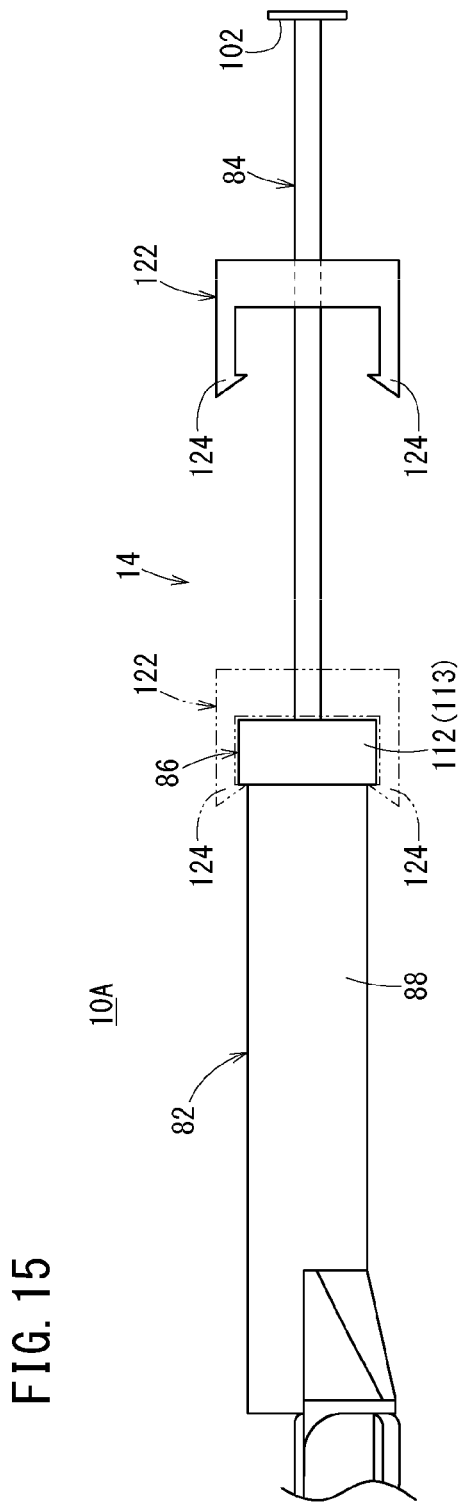
FIG. 15 is a side view of a guide wire unit according to a second modification.

As illustrated in FIG. 15, the guide wire unit 14 may be provided with an excessive insertion inhibition member 122 configured to inhibit excessive insertion of the guide wire 80 into the blood vessel. The excessive insertion inhibition member 122 is configured to be fixable at an arbitrary position in the axial direction of the wire operation member 84 by the user. When the user operates the wire operation member 84 in the distal end direction, the excessive insertion inhibition member 122 also moves in the distal end direction together. Along with the movement, the excessive insertion inhibition member 122 is locked by the proximal end portion of the cover 86, whereby the guide wire 80 is inhibited from further advancing and the excessive insertion is inhibited.

In addition, the excessive insertion inhibition member 122 may have an elastically-deformable engagement arm 124 as illustrated in FIG. 15 in order to grant a function of a guide wire retraction inhibition mechanism to the excessive insertion inhibition member 122. In this case, the excessive insertion inhibition member 122 is locked to the cover 86 as illustrated by an imaginary line, and at the same time, the engagement arm 124 is engaged with the cover 86 or the guide member 82. With this engagement, the wire operation member 84 is inhibited from retracting with respect to the guide member 82. Therefore, it is possible to inhibit the guide wire 80 from unintentionally retracting in the state where the guide wire 80 protrudes from the distal end of the inner needle 20 by an arbitrary protrusion length. Incidentally, the guide wire retraction inhibition mechanism may be fixedly provided at the proximal end portion of the wire operation member 84 instead of the excessive insertion inhibition member 122.

Figure 16:
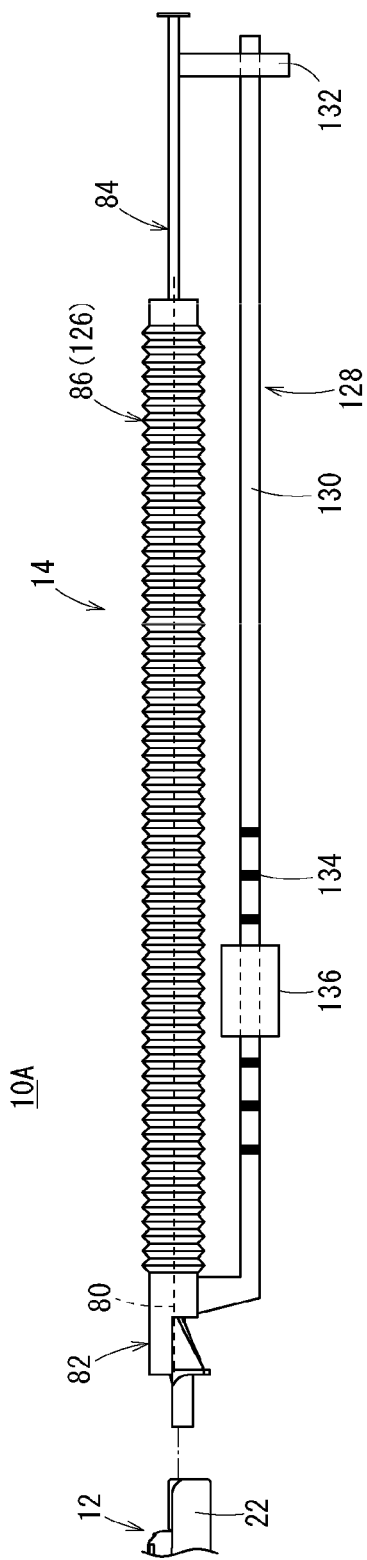
FIG. 16 is a side view of a guide wire unit according to a third modification.

As illustrated in FIG. 16, the cover 86 may be configured using a bellows member 126 stretchable in the axial direction in the guide wire unit 14. A distal end portion of the bellows member 126 is connected to the guide member 82. A proximal end portion of the bellows member 126 may be configured to be similar to the proximal end portion (see FIG. 8) of the third tubular member 108.

In addition, a guide mechanism 128 may be provided to improve straightness of the guide wire 80 as in the guide wire unit 14 illustrated in FIG. 16. The illustrated guide mechanism 128 includes a guide rod 130, which is fixed to the guide member 82 and extends from the guide member 82 in the proximal end direction, and a support portion 132 that is fixed to the wire operation member 84 and slidably supports the guide rod 130.

In this case, the guide rod 130 may be provided with a reference portion 134 (for example, a scale) for confirmation of the protrusion length of the guide wire 80 from the distal end of the inner needle 20. When the user operates the wire operation member 84 in the distal end direction in the state where the bellows member 126 contracts in the axial direction to a maximum extent, it is possible to know the protrusion length of the guide wire 80 from the distal end of the inner needle 20 by viewing the reference portion 134 in relation to the support portion 132.

In addition, the guide rod 130 may be provided with an excessive insertion inhibition member 136 configured to inhibit excessive insertion of the guide wire 80 into the blood vessel. The excessive insertion inhibition member 136 is preferably configured to be fixable at an arbitrary position in the axial direction of the guide rod 130 by the user. When the user operates the wire operation member 84 in the distal end direction in the state where the bellows member 126 contracts in the axial direction to the maximum extent, the support portion 132 is locked by the excessive insertion inhibition member 136. Accordingly, the guide wire 80 is inhibited from further advancing, and the excessive insertion is inhibited Second Embodiment A catheter assembly 10B according to a second embodiment illustrated in FIG. 17 includes a catheter unit 12 and a guide member 140 that is attachable to a proximal end portion of a needle hub 22 and configured to guide a guide wire 80 toward an inner needle 20. The catheter unit 12 in the catheter assembly 10B has the same configuration as the catheter unit 12 in the above-described catheter assembly 10A (see FIG. 1 and the like). A guide wire hub 81 is fixed to a proximal end portion of the guide wire 80.

Figure 18A:
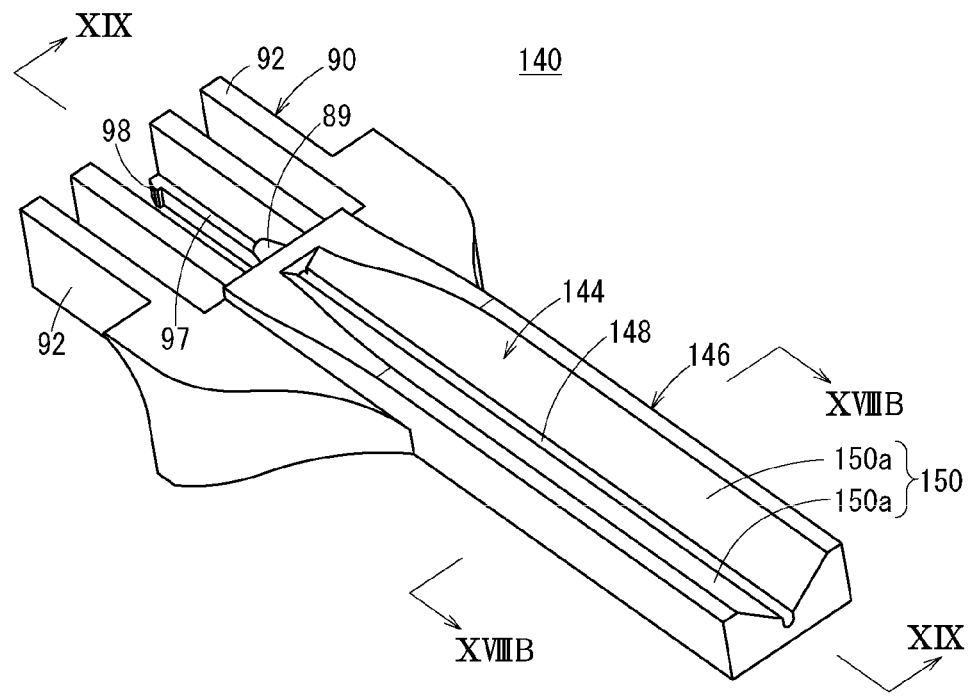
FIG. 18A is a perspective view of a guide member of the catheter assembly illustrated in FIG. 17 as viewed from a proximal end side.

As illustrated in FIG. 18A, the guide member 140 includes a body portion 146 that has a guide groove 144 having a Y-shaped cross section, a second fitting portion 90 (left and right male fitting portions 92) protruding in the distal end direction from a distal end of the body portion 146. The guide groove 144 provided in the body portion 146 has a narrow bottom portion 148 extending straight and an inducing portion 150 that is continuous to the bottom portion 148, is wider than the bottom portion 148, and is open upward.

Figure 18B:
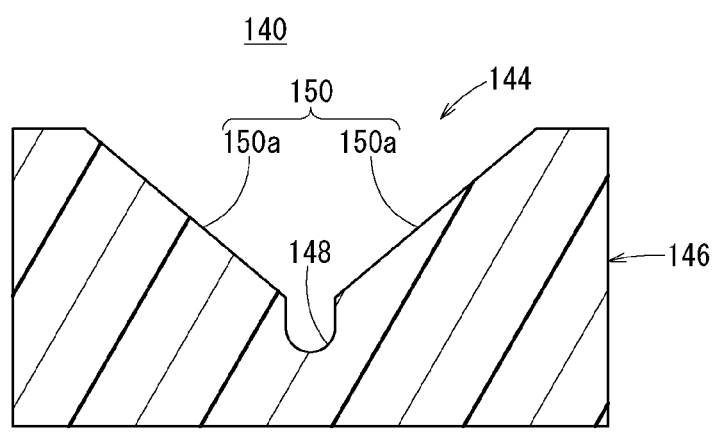
FIG. 18B is a cross-sectional view taken along a line XVIIIB-XVIIIB of FIG. 18A.

The bottom portion 148 is formed so as to be positioned coaxially with a lumen 21 of the inner needle 20 in a state where the guide member 140 is attached to the needle hub 22. As illustrated in FIG. 18B, the inducing portion 150 is open at an upper surface of the guide member 140 and extends parallel to the bottom portion 148. In addition, the inducing portion 150 has left and right inclined surfaces 150a continuous to upper ends of an inner wall of the bottom portion 148, and decreases in width toward the bottom portion 148.

Figure 19:
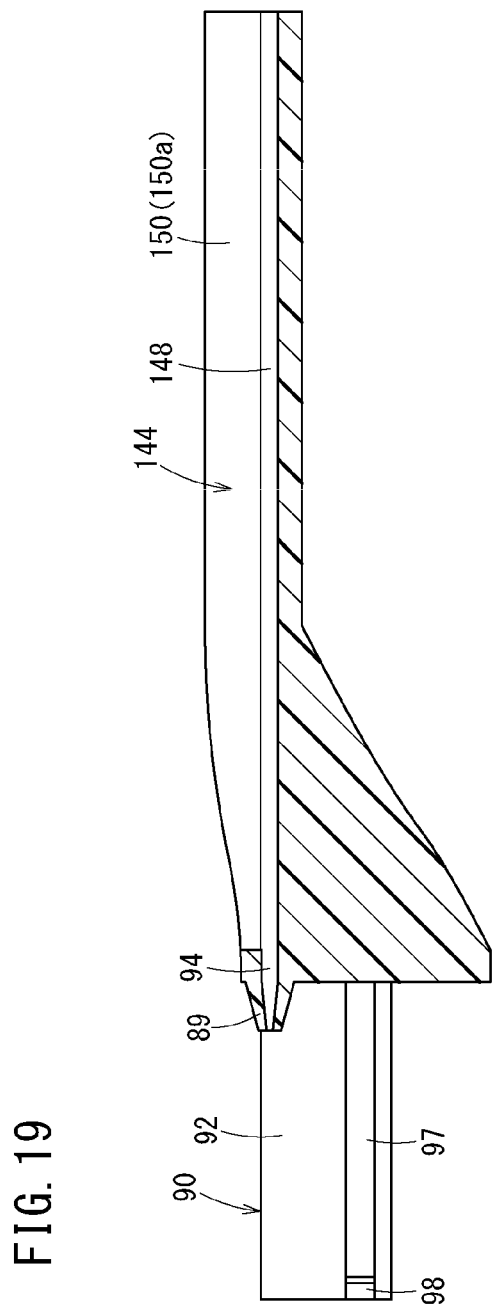
FIG. 19 is a cross-sectional view taken along a line XIX-XIX of FIG. 18A.

In addition, as illustrated in FIG. 19, the guide member 140 has an insertion protrusion 89 in which a wire lead-out hole 94 is formed similarly to the guide member 82 (see FIG. 4 and the like). The wire lead-out hole 94 communicates coaxially with the bottom portion 148.

The second fitting portion 90 of the guide member 140 has the same configuration as the second fitting portion 90 of the guide member 82 described above.

Next, functions and effects of the catheter assembly 10B configured as described above will be described.

At the time of treatment using the catheter assembly 10B, a user determines whether to use the guide wire 80 similarly to the above-described (1) in the method of using the catheter assembly 10A. Then, when it is determined that the use of the guide wire 80 is necessary, the catheter assembly 10B can be used, for example, according to the following procedure.

Figure 20:
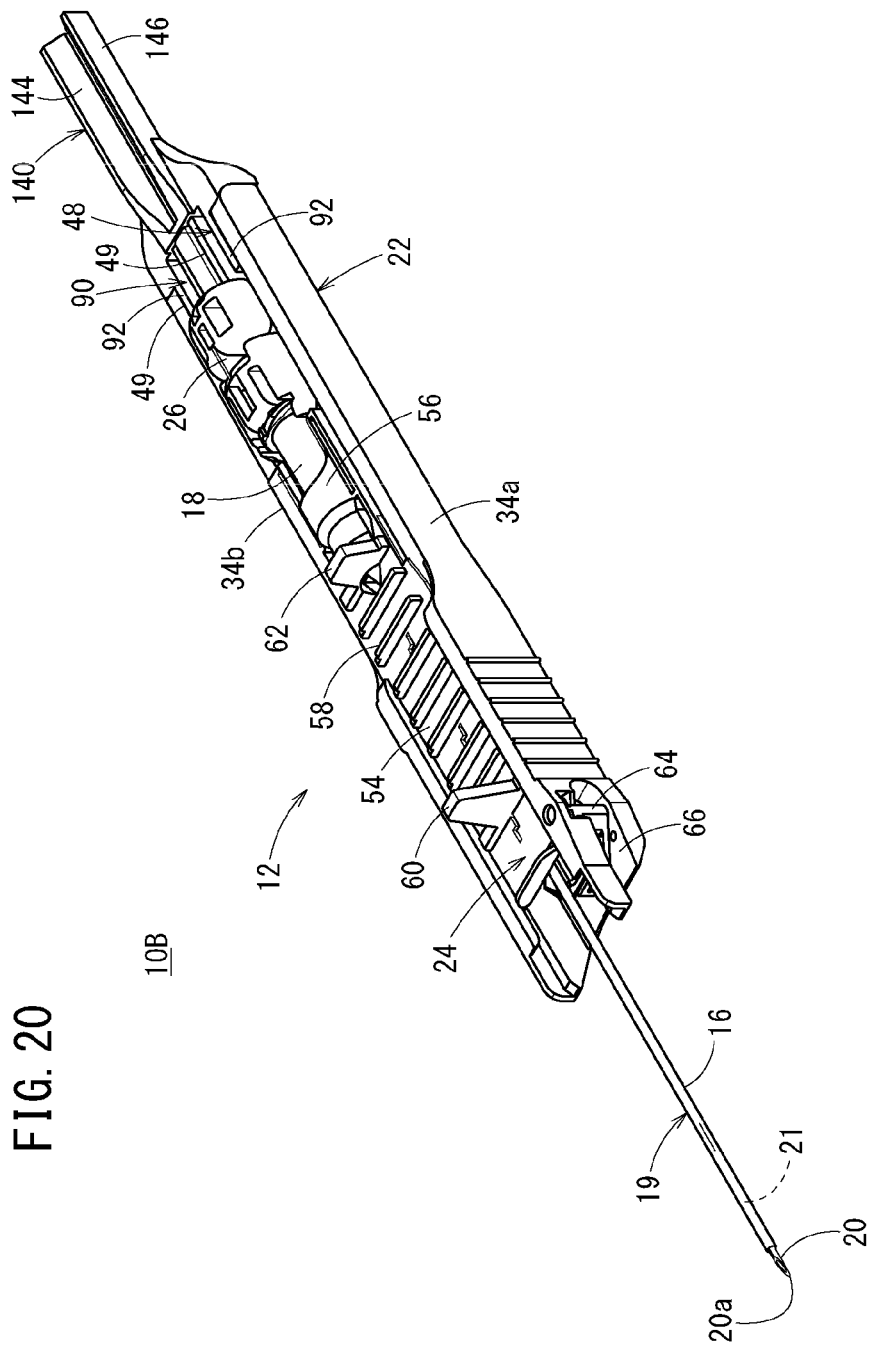
FIG. 20 is a first view for describing a method of using the catheter assembly illustrated in FIG. 17.

As illustrated in FIG. 20, the user attaches the guide member 140 to the proximal end portion of the needle hub 22 of the catheter unit 12 in an initial state. Specifically, the second fitting portion 90 provided in the guide member 140 is fitted to a first fitting portion 48 provided at the proximal end portion of the needle hub 22 through a proximal end opening of left and right female fitting portions 49 (see FIG. 20).

Next, as illustrated in FIG. 21A, the user places a distal end of the guide wire 80 on the guide groove 144 of the guide member 140. Then, the distal end of the guide wire 80 enters the bottom portion 148 of the guide groove 144 and is positioned coaxially with the lumen 21 of the inner needle 20. At this time, the distal end of the guide wire 80 is guided smoothly to the bottom portion 148 along the inclined surface 150a of the inducing portion 150 even if the user does not intend to accurately align a distal end position of the guide wire 80 with the bottom portion 148. Thus, the distal end of the guide wire 80 is easily positioned at the coaxial position with the lumen 21 of the inner needle 20.

Next, the user moves the guide wire 80 in the distal end direction with respect to the guide member 140, thereby inserting the guide wire 80 into the lumen 21 of the inner needle 20 as illustrated in FIG. 21B. At this time, the distal end of the guide wire 80 moves from the bottom portion 148 of the guide member 140 to the wire lead-out hole 94 (see FIG. 19), and is further led out in the distal end direction from the wire lead-out hole 94 to be inserted into the lumen 21 of the inner needle 20. During this insertion operation, for example, the user causes the distal end of the guide wire 80 to be positioned at the lumen 21 of the distal end portion of the inner needle 20 (a zero protrusion length position) as illustrated in FIG. 22.

Next, the user performs a puncturing operation to puncture a skin of a patient with the catheter unit 12 similarly to the above-described (4) in the method of using the catheter assembly 10A. Next, the user moves the guide wire 80 in the distal end direction with respect to the guide member 140, thereby moving the guide wire 80 in the distal end direction. Accordingly, the guide wire 80 protrudes from the distal end of the inner needle 20 by a predetermined length, and the distal end of the guide wire 80 is inserted to a target position in a blood vessel.

Thereafter, operations in the above-described (6) to (9) are performed in the same manner as the method of using the catheter assembly 10A.

Meanwhile, when it is determined that the use of the guide wire 80 is unnecessary at the time of using the catheter assembly 10B, only the catheter unit 12 is used. A use method at this time is the same as the above-described method of using the catheter unit 12 in the case of not using the guide wire 80 in the catheter assembly 10A.

As described above, according to the catheter assembly 10B, the guide member 140 and the guide wire 80 are not used when a catheter 16 is indwelled in a patient for which the catheter is likely to be simply indwelled, and thus, the operation thereof is simple, the operation is easy to learn, and the device is also compact. In addition, when the catheter 16 is indwelled in a patient for which the catheter is likely to be hardly indwelled, it is possible to perform smooth indwelling by attaching the guide member 140 to the needle hub 22 and using the guide wire 80. In this manner, it is possible to enjoy advantages of both the cases by selecting whether to use the guide wire 80 depending on a situation.

In particular, the guide member 140 has the guide groove 144 in which the bottom portion 148 and the inducing portion 150 are formed in the present embodiment. With this configuration, when the guide wire 80 is placed in the guide groove 144, the distal end of the guide wire 80 is induced to the bottom portion 148 by the inducing portion 150, and the distal end of the guide wire 80 is guided toward the lumen 21 of the inner needle 20 at the bottom portion 148. Therefore, it is possible to smoothly insert the guide wire 80 into the lumen 21 of the inner needle 20.

In the present embodiment, the guide member 140 and the guide wire 80 are combined at the time of use. Therefore, the guide wires 80 with various specifications (lengths, thicknesses, distal end shapes (straight or J-shaped), elasticity, and the like) are prepared, and it is possible to select and use the guide wire 80 desired by the user. In addition, in the present embodiment, the guide wire 80 used in combination with the guide member 140 is not a dedicated item for the guide member 140, but can be freely selected from general-purpose guide wires.

Figure 23:
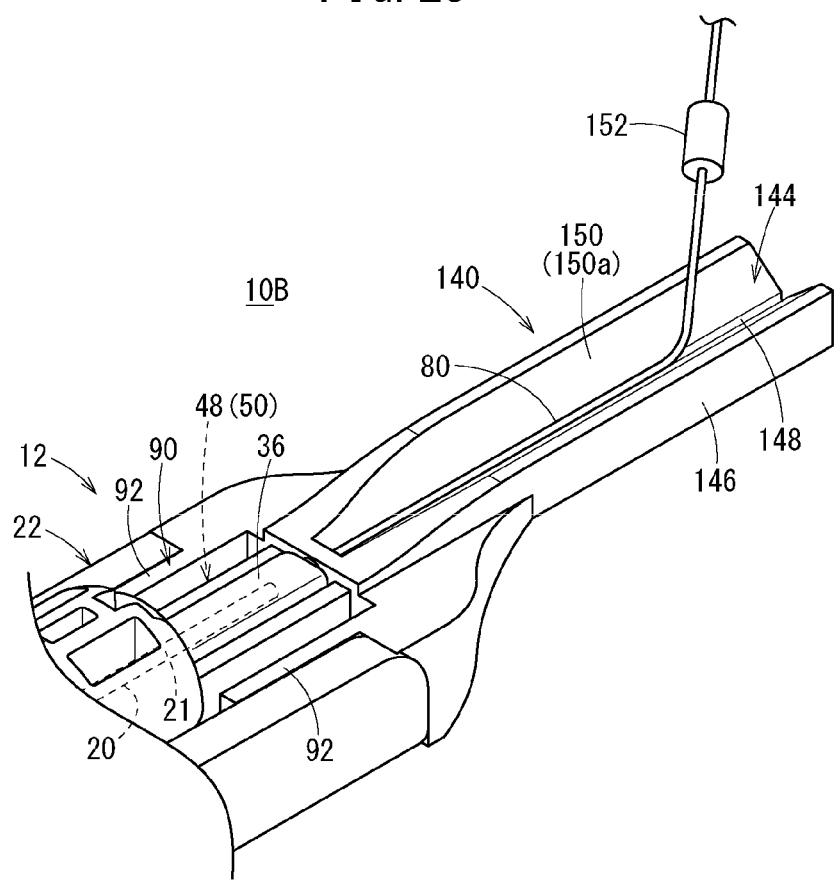
FIG. 23 is a perspective view illustrating a modification in which a guide wire is provided with an excessive insertion inhibition member.

As illustrated in FIG. 23, the excessive insertion inhibition member 152, configured to inhibit the excessive insertion of the guide wire 80 into the blood vessel, may be attached to the guide wire 80. When the user moves the guide wire 80 in the distal end direction with respect to the guide member 140 in order to insert the guide wire 80 into the blood vessel, the excessive insertion inhibition member 152 is locked by the guide member 140. Accordingly, the guide wire 80 is inhibited from further moving in the distal end direction, and the excessive insertion is inhibited.

The excessive insertion inhibition member 152 may be configured to be fixable at an arbitrary position on the guide wire 80 by the user. For example, a clamp configured to switch opening and closing of a tube is attached to a tube in an infusion set or the like, and such a clamp can be fixed at an arbitrary position of the tube. Therefore, it is possible to attach the excessive insertion inhibition member 152 to an arbitrary position on the guide wire 80 by configuring the excessive insertion inhibition member 152 in the same manner as the clamp.

As illustrated in FIG. 24, a guide wire retraction inhibition portion 154 may be provided on the guide wire 80. In FIG. 24, the guide wire retraction inhibition portion 154 is formed integrally with the guide wire hub 81, and has an elastically-deformable engagement arm 156. A protrusion 158 with which the engagement arm 156 can be engaged is provided at a proximal end portion of the guide member 140. A groove with which the engagement arm 156 can be engaged may be provided instead of the protrusion 158.

As the engagement arm 156 is engaged with the guide member 140 to perform locking, the guide wire 80 is inhibited from retracting with respect to the guide member 140. Therefore, it is possible to inhibit the unintentional retraction of the guide wire 80 in the state where the guide wire 80 protrudes from the distal end of the inner needle 20 by an arbitrary protrusion length. Incidentally, a guide wire retraction inhibition function may be granted to the excessive insertion inhibition member 152 by providing the engagement arm similar to the engagement arm 156 in the above-described excessive insertion inhibition member 152 (see FIG. 23).

Figure 25A:
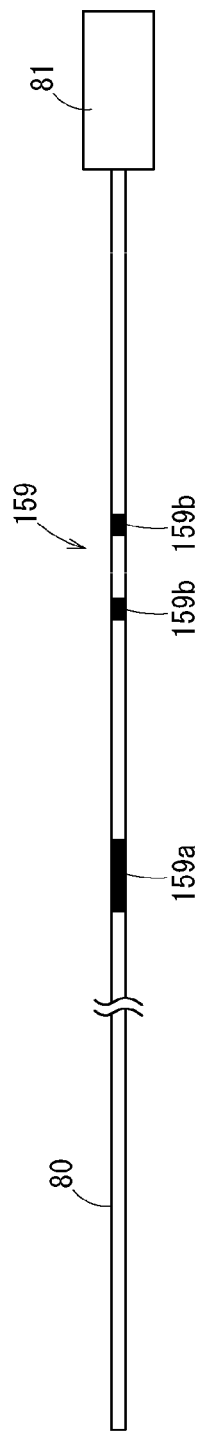
FIG. 25A is a side view illustrating a modification in which a guide wire is provided with a reference portion.

As illustrated in FIG. 25A, a reference portion 159, configured to indicate a distal end position of the guide wire 80 with respect to the distal end of the inner needle 20 may be provided on an outer surface of the guide wire 80. The reference portion 159 notifies the user of the distal end position of the guide wire 80 with respect to the distal end of the inner needle 20 based on a positional relationship with the guide member 140. The reference portion 159 may include a marker 159a indicating the zero protrusion length position of the guide wire 80 and a plurality of markers 159b each of which indicates a protrusion length of the guide wire 80 from the inner needle 20.

Figure 25B:
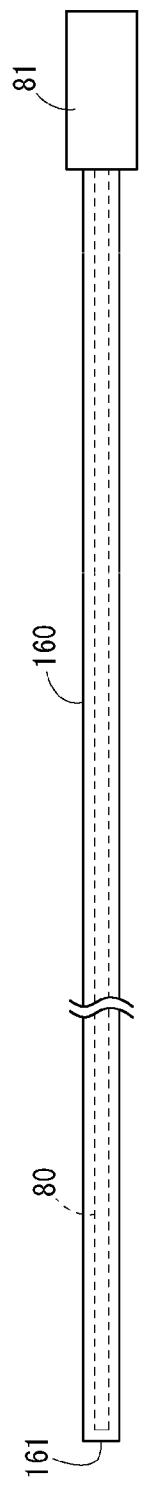
FIG. 25B is a side view illustrating a modification in which a cover that covers a guide wire is provided.

As illustrated in FIG. 25B, a cover 160 may be attached to the guide wire 80. The cover 160 is formed in a hollow shape so as to house the guide wire 80. The cover 160 may have a length that enables covering up to the distal end of the guide wire 80 in the initial state, or may have a length that causes the guide wire 80 to protrude from a distal end opening 161 by a predetermined length in the initial state. As this cover 160 is provided, the guide wire 80 is covered by the cover 160 in the initial state, and thus, it is possible to inhibit contamination of the guide wire 80.

Figure 26:
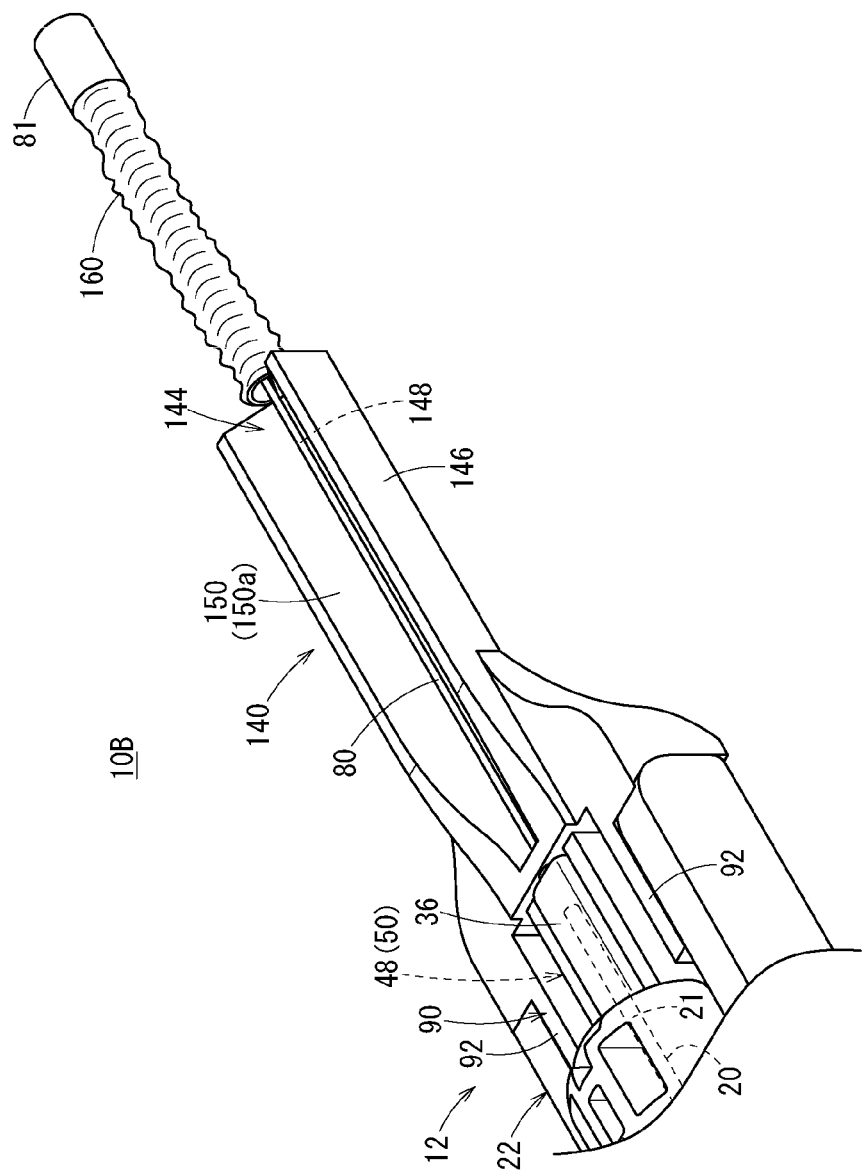
FIG. 26 is a perspective view illustrating a cover contracted in the axial direction along with insertion of a guide wire.

As illustrated in FIG. 26, the cover 160 may be configured to be soft such that a distal end of the cover is compressed by being pushed in the proximal end direction along with insertion of the guide wire 80 into the inner needle 20 via the guide member 140. With this configuration, the cover 160 contracts along with the insertion of the guide wire 80, and thus, it is possible to insert the guide wire 80 without any problem.

Figure 27:
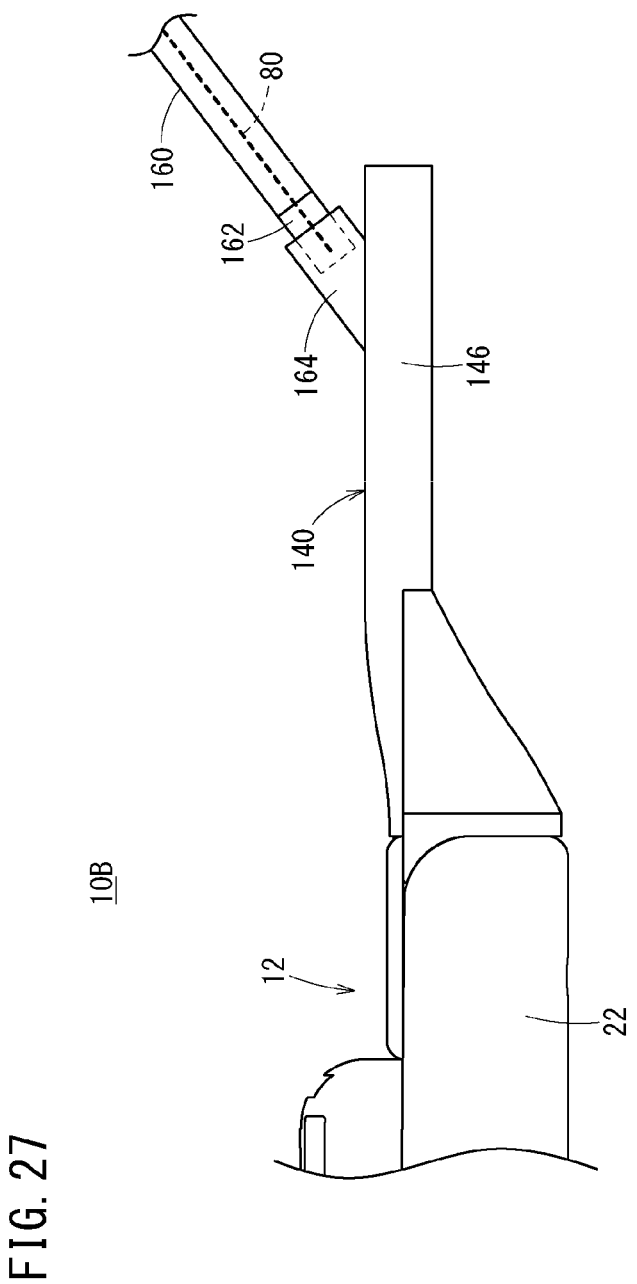
FIG. 27 is a side view illustrating a modification in which a connector is provided at a distal end portion of a cover.

As illustrated in FIG. 27, a connector 162 configured to be connectable to the guide member 140 may be provided at the distal end of the cover 160. The connector 162 is configured to be inclined with respect to the guide member 140 such that a distal end thereof faces the guide groove 144 in the state of being connected to the guide member 140. The guide member 140 is provided with a fitting portion 164 into which the connector 162 can be fitted. For example, the connector 162 is taper-fitted to the fitting portion 164. The connector 162 may be fitted to the fitting portion 164 in a straight manner.

Incidentally, a modification of the cover 160 covering the guide wire 80 may be a tube that is configured in a spiral shape for the sake of compactness.

Figure 28:
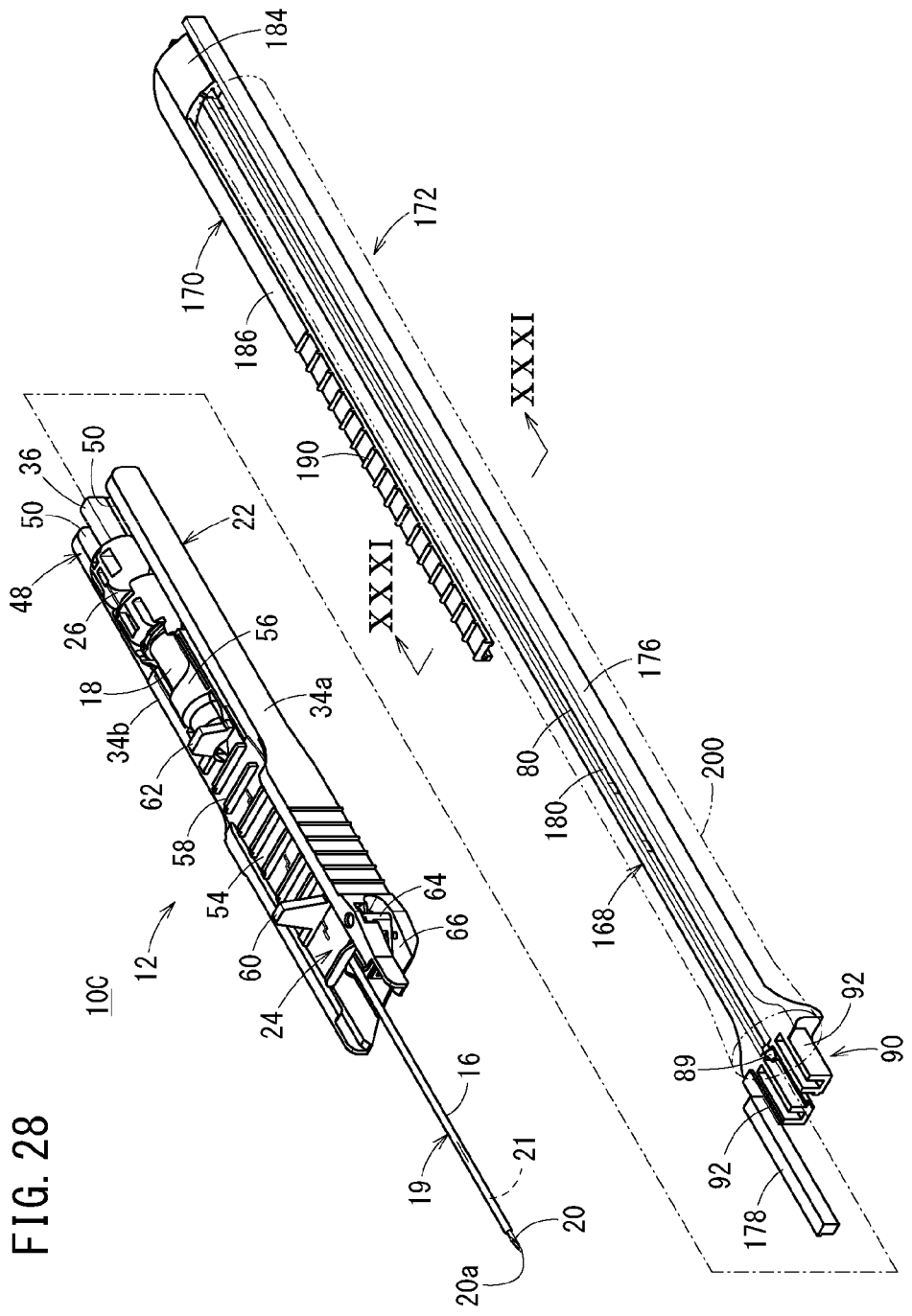
FIG. 28 is a perspective view of a catheter assembly according to a third embodiment.

Incidentally, the same or similar functions and effects as those of the first embodiment can be obtained in the second embodiment for common parts with the first embodiment Third Embodiment A catheter assembly 10C according to a third embodiment illustrated in FIG. 28 includes a catheter unit 12 forming a main part of the catheter assembly 10C and a guide wire unit 172 that can be attached to the catheter unit 12 and has a guide wire 80, a guide member 168, and a wire operation member 170.

Figure 29:
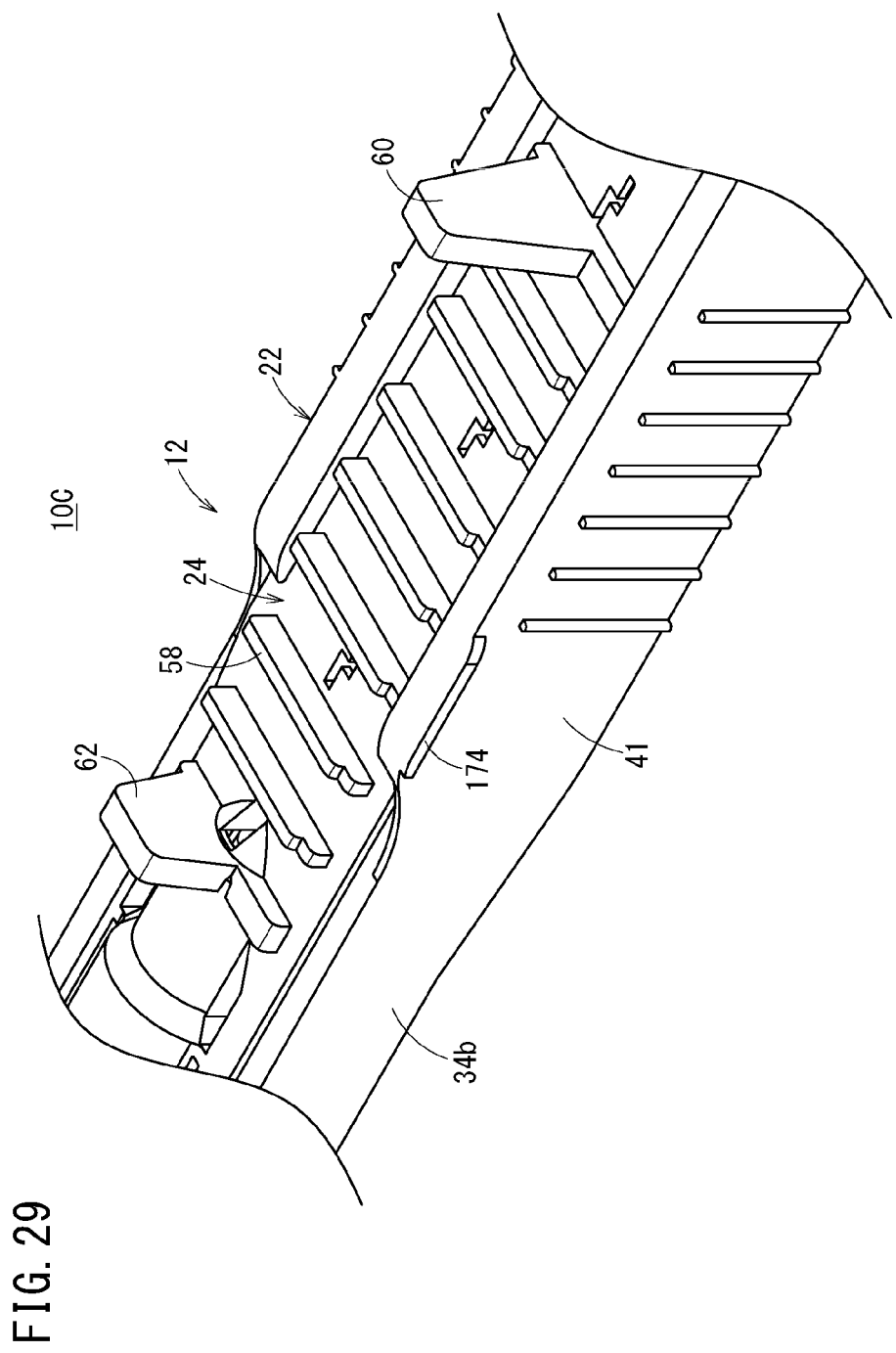
FIG. 29 is a perspective view illustrating a guide rib provided on a needle hub.

As illustrated in FIG. 29, a needle hub 22 of the catheter unit 12 is provided with guide ribs 174 (guide portions) laterally protruding and extending in the axial direction. The guide rib 174 is configured so as to slidably support and guide the wire operation member 170 in the axial direction at the time of moving the wire operation member 170 forward with respect to the needle hub 22 in order to cause a distal end of the guide wire 80 to protrude from a distal end of an inner needle 20 by a predetermined length. The illustrated guide rib 174 protrudes rightward from an upper portion of the proximal end of a distal-end-side region 41 of a right sidewall 34b.

The guide wire unit 172 and the catheter unit 12 are separated from each other as illustrated in FIG. 28 in the state of the catheter assembly 10C provided as a product. The guide wire unit 172 includes the guide wire 80, the guide member 168, which is attachable to a proximal end portion of the needle hub 22 and guides the guide wire 80, and the wire operation member 170, which is fixed to a proximal end portion of the guide wire 80 and supported by the guide member 168 so as to be axially slidable.

Figure 30:
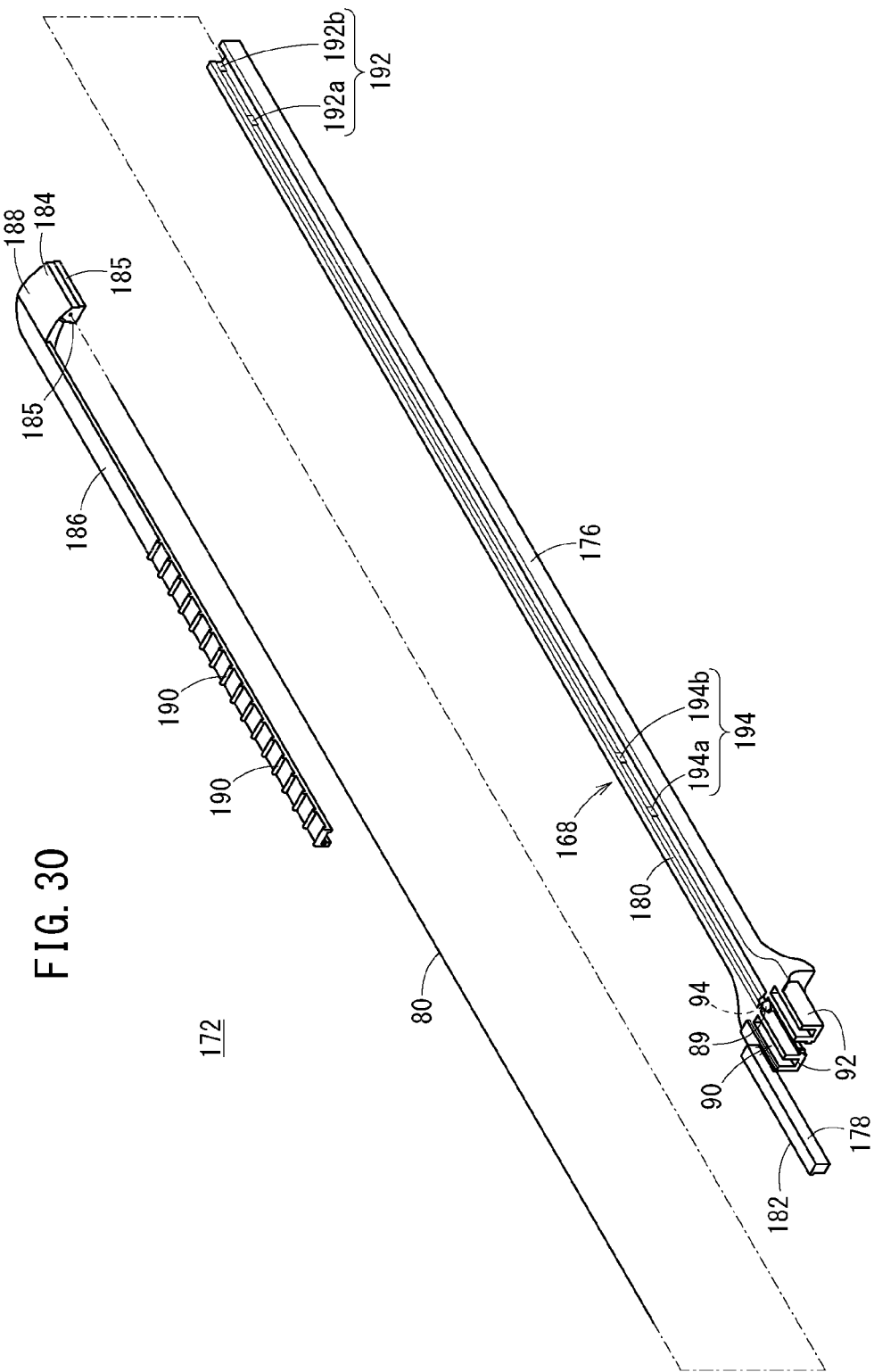
FIG. 30 is an exploded perspective view of a guide wire unit of the catheter assembly illustrated in FIG. 28.

In FIG. 30, the guide member 168 is configured to guide the guide wire 80 toward the inner needle 20. Specifically, the guide member 168 includes a body portion 176 extending straight, a second fitting portion 90 that has a plurality (two) of male fitting portions 92 protruding in the distal end direction from a distal end of the body portion 176, and a guide rail 178 extending in the distal end direction from the distal end of the body portion 176.

The body portion 176 is provided with not only an insertion protrusion 89 in which a wire lead-out hole 94 is provided at a distal end portion thereof but also a slide groove 180 extending straight along the longitudinal direction of the body portion 176. The slide groove 180 in the illustrated example is open at an upper surface and a proximal end surface of the body portion 176.

Figure 31:
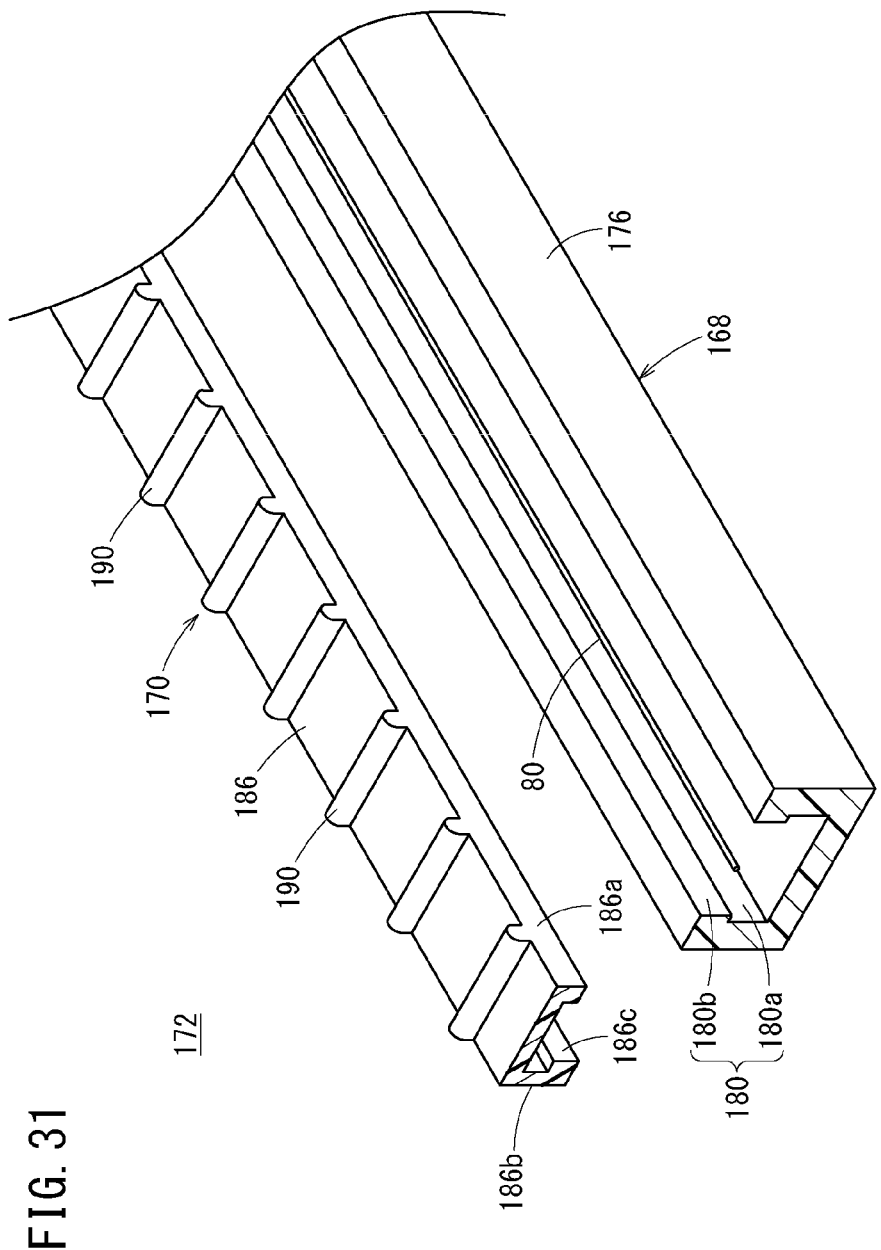
FIG. 31 is a cross-sectional view taken along a line XXXI-XXXI of FIG. 28.

A distal end of the slide groove 180 is positioned at the distal end portion of the body portion 176 and communicates with the wire lead-out hole 94. As illustrated in FIG. 31, each upper portion of left and right sidewalls forming the slide groove 180 slightly protrudes inward, whereby the slide groove 180 has a lower portion 180a having a relatively wide width and an upper portion 180b having a relatively narrow width.

In FIG. 30, the guide member 168 is longer than the entire length of the guide wire 80. The guide wire 80 is housed inside the body portion 176 in the guide wire unit 172 in the initial state. The distal end of the guide wire 80 is arranged in the wire lead-out hole 94, and the other portion of the guide wire 80 is arranged in the slide groove 180.

The guide rail 178 is configured to axially overlap the needle hub 22 in the state where the guide member 168 is attached to the needle hub 22 and to slidably support and guide the wire operation member 170 in the axial direction. The guide rail 178 in the illustrated example extends in parallel with the male fitting portion 92 and protrudes to the distal end side more than the male fitting portion 92.

Figure 33:
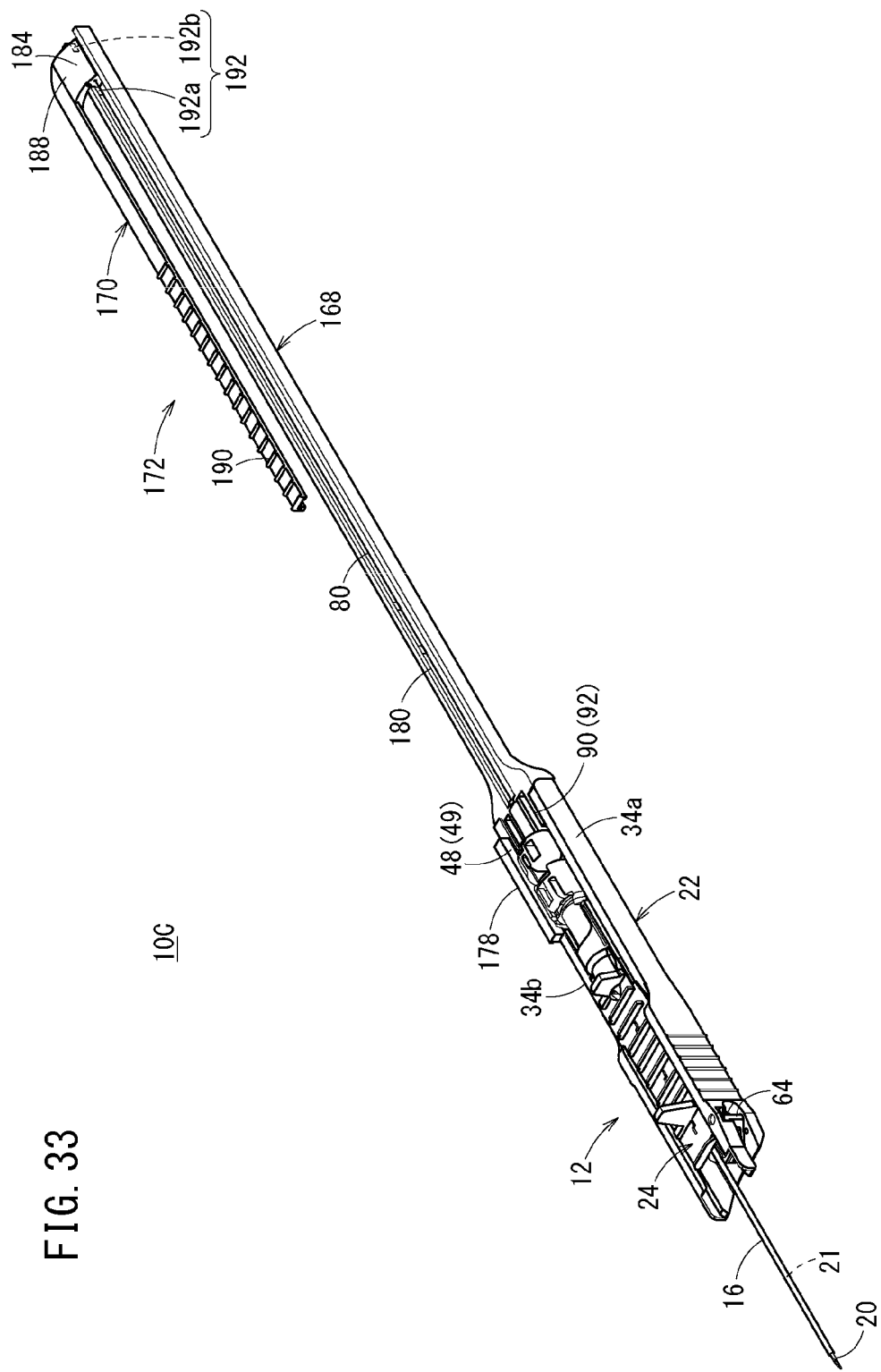
FIG. 33 is a first view for describing a method of using the catheter assembly illustrated in FIG. 28.

In the state where the guide member 168 is attached to the needle hub 22, the guide rail 178 is placed on an upper surface of the right sidewall 34b of the needle hub 22 (see FIG. 33). Accordingly, the guide rail 178 is supported from the lower side by the upper surface. In FIG. 30, the guide rail 178 is provided with a protrusion 182 that laterally protrudes and extends along the longitudinal direction of the guide rail 178.

The wire operation member 170 has a slide portion 184 engaged with the guide member 168 so as to be axially slidable and an extension portion 186 extending in the distal end direction from the slide portion 184. Bulging portions 185 protruding laterally outward are formed on both left and right sides of a lower portion of the slide portion 184. As the bulging portion 185 is fitted to the lower portion 180a of the slide groove 180, the slide portion 184 is inhibited from being withdrawn upward from the slide groove 180.

In the wire operation member 170 in the illustrated example, the extension portion 186 is provided at a position shifted from the slide portion 184 in the lateral direction, and the extension portion 186 and the slide portion 184 are integrally connected via a connecting portion 188. A large number of ribs 190 are provided with a space therebetween on an upper surface of the extension portion 186 in order to inhibit slippage at the time of being touched and operated by the user's finger.

As illustrated in FIG. 31, protruding portions 186a and 186b protruding downward are provided at both end edges in the width direction of the extension portion 186. A rib 186c protruding inward is provided at a lower end of the protruding portion 186b on the right side. When the extension portion 186 slides on the guide rail 178 (see FIG. 30), the protruding portions 186a and 186b oppose left and right upper portions of the guide rail 178, and the rib 186c is engaged with the protrusion 182 provided on the guide rail 178. Accordingly, the extension portion 186 is guided straight along the guide rail 178.

In a state (see FIG. 34) where the guide member 168 is attached to the needle hub 22 and the distal end of the guide wire 80 is positioned in the lumen 21 in a distal end portion of the inner needle 20, the most distal end portion of the extension portion 186 is positioned on the distal side of the most proximal end portion of the needle hub 22, and is preferably positioned on the distal end side of a central portion in the longitudinal direction of the needle hub 22.

As illustrated in FIG. 30, the guide member 168 may be provided with an initial position temporary fixing portion 192. In the initial state of the guide wire unit 172, the wire operation member 170 is releasably fixed to the guide member 168 at the proximal end portion of the guide member 168 by the initial position temporary fixing portion 192. In the present embodiment, the initial position temporary fixing portion 192 has two protrusions 192a and 192b provided in a proximal end portion of the slide groove 180 with a space therebetween in the axial direction.

In the initial state, the protrusion 192a on the distal end side is releasably engaged with a corner of a distal end of the slide portion 184, and the protrusion 192b on the proximal end side is engaged with a corner of a proximal end of the slide portion 184. Accordingly, the wire operation member 170 is temporarily fixed at an initial position with respect to the guide member 168.

In addition, the guide member 168 may be provided with an intermediate position temporary fixing portion 194. The intermediate position temporary fixing portion 194 releasably fixes the wire operation member 170 to the guide member 168 at an intermediate position where the guide wire 80 is arranged at a zero protrusion length position. In the present embodiment, the intermediate position temporary fixing portion 194 has two protrusions 194a and 194b provided in an intermediate portion of the slide groove 180 with a space therebetween in the axial direction.

When the wire operation member 170 is moved in the distal end direction with respect to the guide member 168 so as to move the guide wire 80 to the zero protrusion length position, the protrusion 194a on the distal end side is releasably engaged with the corner of the distal end of the slide portion 184 and the protrusion 194b on the proximal end side is releasably engaged with the corner of the proximal end of the slide portion 184.

Figure 32:
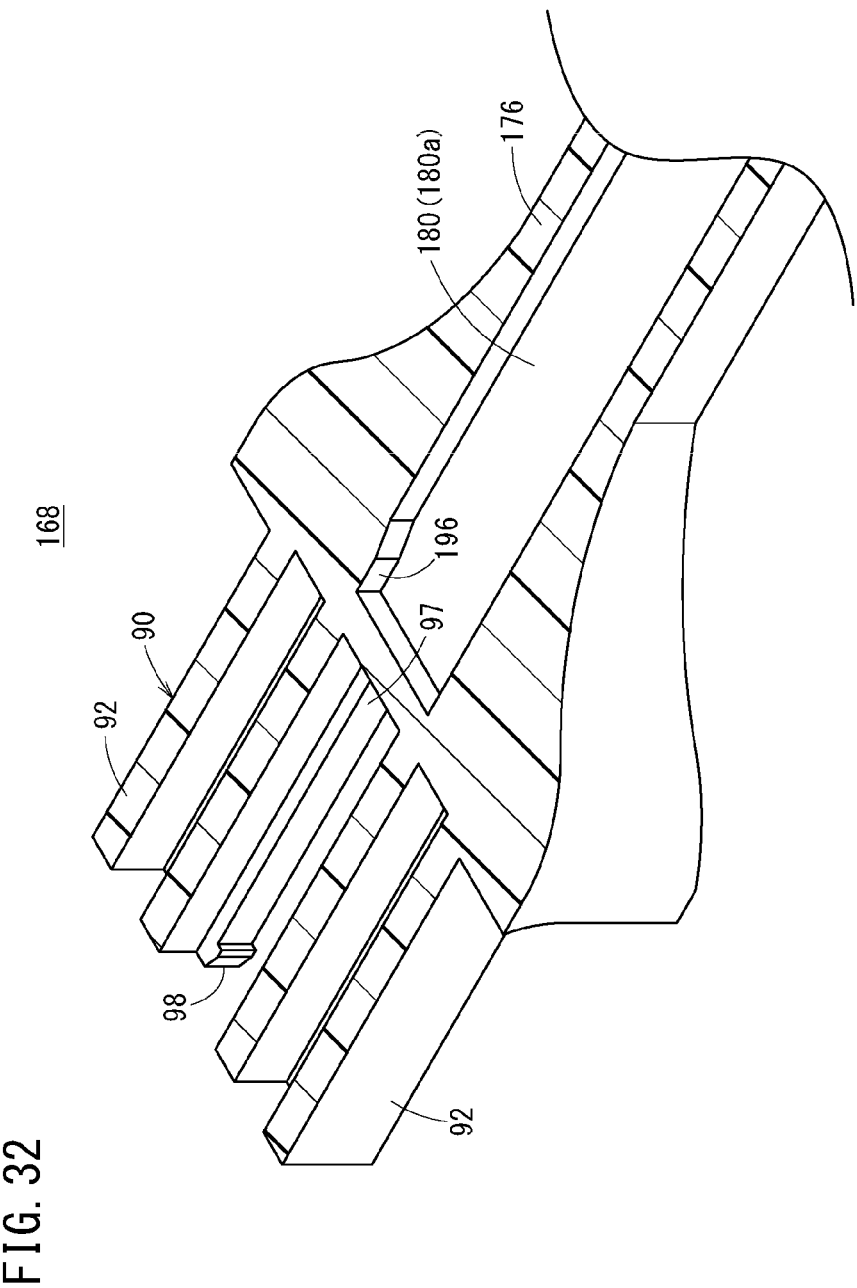
FIG. 32 is a perspective cross-sectional view of a distal end portion of a guide member.

The guide wire unit 172 may be provided with a guide wire retraction inhibition mechanism that is configured to suppress movement of the wire operation member 170 in the proximal end direction with respect to the guide member 168 when the guide wire 80 protrudes from the distal end of the inner needle 20 by a predetermined length. For example, as illustrated in FIG. 32, the guide wire retraction inhibition mechanism may have a form of a bulging portion 196 that is provided in the distal end portion of the slide groove 180 and bulges inward in the width direction of the slide groove 180. The distal end portion of the slide groove 180 has a narrower width than a portion thereof on the proximal end side of the bulging portion 196 since the bulging portion 196 is provided.

The distal end portion of the slide portion 184 is fitted to the distal end portion of the slide groove 180 as the wire operation member 170 is moved in the distal end direction with respect to the guide member 168 to a position where the guide wire 80 protrudes from the distal end of the inner needle 20 by the predetermined length. Accordingly, it is possible to inhibit the guide wire 80 from unintentionally retracting in the state where the guide wire 80 protrudes from the distal end of the inner needle 20 by an arbitrary protrusion length.

Incidentally, since a side surface of the bulging portion 196 is parallel to a movable direction (axial direction) of the slide portion 184 in the illustrated example, a fitting form of the slide portion 184 at the distal end portion of the slide groove 180 is straight-fitting. The fitting form of the slide portion 184 at the distal end portion of the slide groove 180 may be tapered-fitting, instead of the straight-fitting, by forming the side surface of the bulging portion 196 in a tapered shape such that the width at the distal end portion of the slide groove 180 decreases in the distal end direction.

Next, functions and effects of the catheter assembly 10C configured as described above will be described.

At the time of treatment using the catheter assembly 10C, a user determines whether to use the guide wire 80 similarly to the above-described (1) in the method of using the catheter assembly 10A. Then, when it is determined that the use of the guide wire 80 is necessary, the catheter assembly 10B can be used, for example, according to the following procedure.

(2c) Attachment of Guide Wire Unit

As illustrated in FIG. 33, the user attaches the guide wire unit 172 in the initial state to the catheter unit 12 in the initial state. Specifically, the second fitting portion 90 provided in the guide member 168 is fitted to a first fitting portion 48 provided at the proximal end portion of the needle hub 22 through a proximal end opening of female fitting portions 49 (see FIG. 28).

(3c) Position Setting of Guide Wire Distal End

Figure 34:
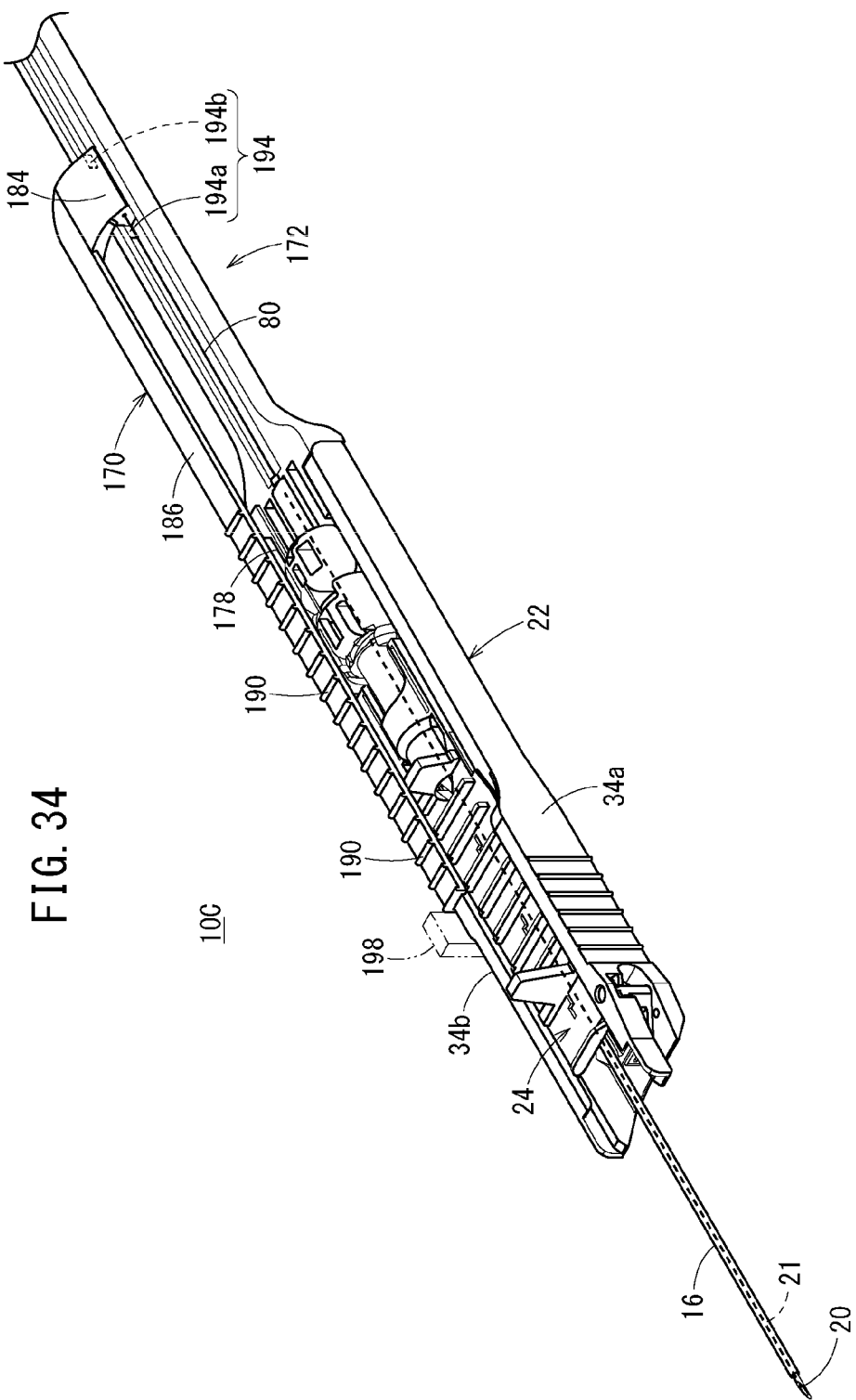
FIG. 34 is a second view for describing the method of using the catheter assembly illustrated in FIG. 28.

Next, the guide wire 80 is introduced into the lumen 21 of the inner needle 20 by operating the guide wire unit 172, and the distal end of the guide wire 80 is arranged in the lumen 21 (the zero protrusion length position) of the distal end portion of the inner needle 20. Specifically, as illustrated in FIG. 34, the guide wire 80 is moved in the distal end direction by moving the wire operation member 170 in the distal end direction with respect to the guide member 168.

At that time, an operating force in the distal end direction with respect to the wire operation member 170 exceeds a fixing force of the initial position temporary fixing portion 192 (see FIG. 33), and the slide portion 184 moves over the protrusion 192a on the distal end side of the initial position temporary fixing portion 192 in the distal end direction. In addition, the distal end of the guide wire 80 moves from the wire lead-out hole 94 (see FIG. 30) to the lumen 21 of the inner needle 20 through the wire introduction hole 46 (see FIG. 4), and advances in the distal end direction in the lumen 21 of the inner needle 20.

When the wire operation member 170 moves in the distal end direction with respect to the guide member 168, the extension portion 186 is placed on the guide rail 178 and is guided in the axial direction by the guide rail 178. Thus, the extension portion 186 does not shake to the right and left or up and down, and the wire operation member 170 can be stably moved in the distal end direction with respect to the guide member 168.

Then, when the slide portion 184 reaches the intermediate position temporary fixing portion 194, the slide portion 184 is temporarily fixed by the intermediate position temporary fixing portion 194. That is, the distal end corner portion of the slide portion 184 is locked to the protrusion 194a on the distal end side and the proximal end corner portion of the slide portion 184 is locked to the protrusion 194b on the proximal end side, and thus movement of the slide portion 184 in the distal end direction and the proximal end direction is suppressed. Accordingly, the movement of the wire operation member 170 with respect to the guide member 168 is restricted in the state where the distal end of the guide wire 80 is arranged at the zero protrusion length position, and unintentional protrusion or retraction of the guide wire 80 is suppressed.

Next, the user performs a puncturing operation to puncture the skin of the patient with the catheter unit 12 similarly to the above-described (4).

(5c) Guide Wire Advancing Operation

Figure 35:
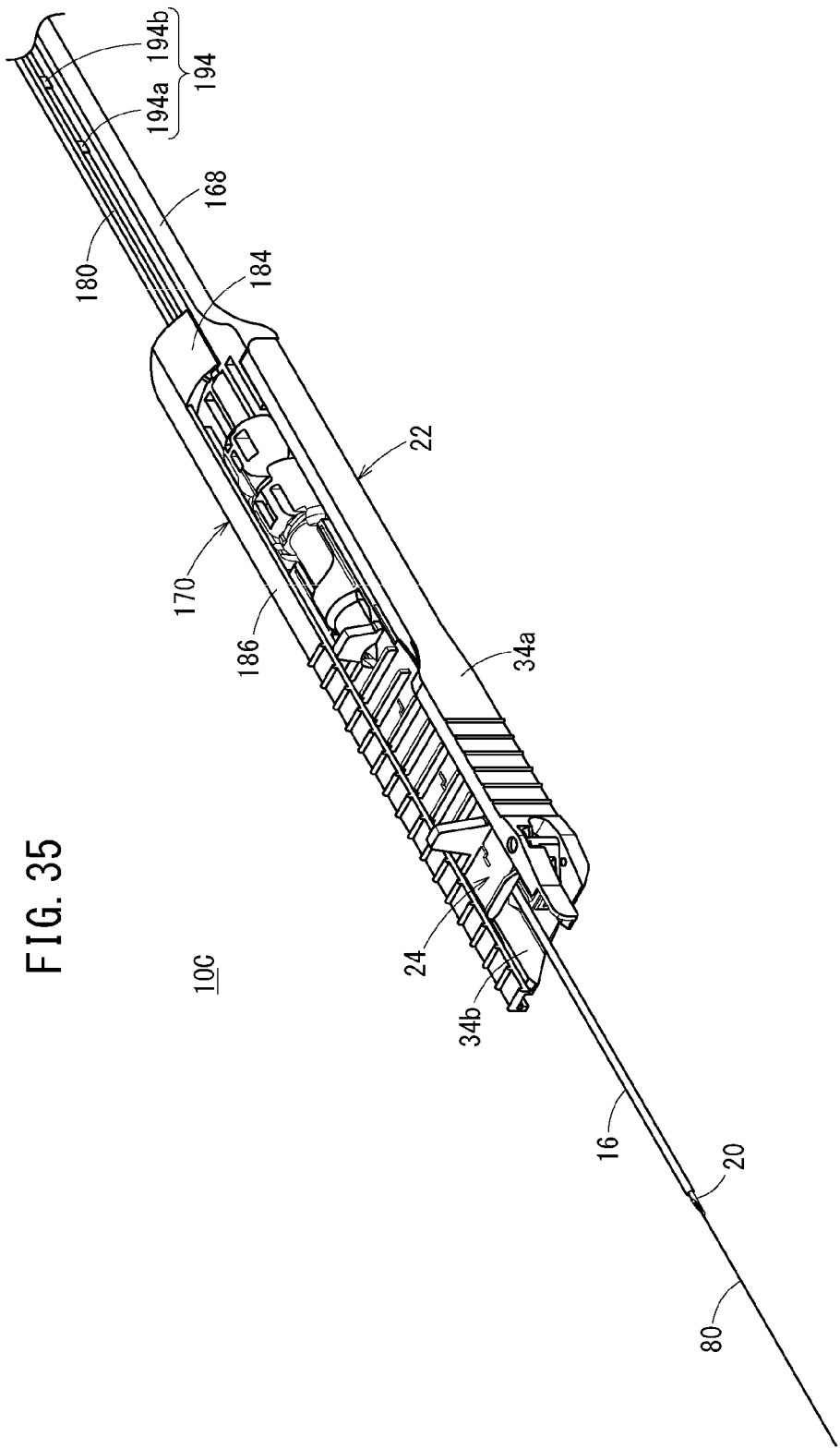
FIG. 35 is a third view for describing the method of using the catheter assembly illustrated in FIG. 28.

Next, the user moves the wire operation member 170 in the distal end direction with respect to the guide member 168 while holding the position of the needle hub 22 in the state where the skin is punctured with the inner needle 20 and the distal end of the catheter 16. Accordingly, the guide wire 80 is caused to protrude from the distal end of the inner needle 20 by a predetermined length as illustrated in FIG. 35.

At that time, the operating force in the distal end direction with respect to the wire operation member 170 exceeds a fixing force of the intermediate position temporary fixing portion 194, and the slide portion 184 moves over the protrusion 194a on the distal end side of the intermediate position temporary fixing portion 194 in the distal end direction. The extension portion 186 slides in the distal end direction while being supported on the upper surface of the right sidewall 34b of the needle hub 22. At this time, since the extension portion 186 is guided in the axial direction by the guide rib 174 (see FIG. 29) provided on the needle hub 22, the wire operation member 170 can be stably moved in the distal end direction. As the guide wire 80 protrudes from the distal end of the inner needle 20, the distal end portion of the guide wire 80 is inserted into a target position in a blood vessel.

The subsequent operations of the catheter assembly 10C may be performed in the same manner as the operations of the above-described (6) to (9) in the method of using the catheter assembly 10A.

Meanwhile, when it is determined that the use of the guide wire 80 is unnecessary in the catheter assembly 10C, only the catheter unit 12 is used. A use method at this time is the same as the above-described method of using the catheter unit 12 in the case of not using the guide wire 80 in the catheter assembly 10A.

As described above, according to the catheter assembly 10C, the guide wire unit 172 is not used when the catheter 16 is indwelled in a patient for which the catheter is likely to be simply indwelled, and thus, the operation thereof is simple, the operation is easy to learn, and the device is also compact. In addition, when the catheter 16 is indwelled in a patient for which the catheter is likely to be hardly indwelled, it is possible to perform smooth indwelling by attaching the guide member 168 to the needle hub 22 and using the guide wire 80. In this manner, it is possible to enjoy advantages of both the cases by selecting whether to use the guide wire 80 depending on a situation.

In particular, since the wire operation member 170 is slidably supported by the guide member 168 in the axial direction in the present embodiment, it is possible to easily perform the operation of causing the guide wire 80 to advance toward the inner needle 20 and the operation of causing the guide wire 80 to protrude from the distal end of the inner needle 20.

In the present embodiment, in the state where the guide member 168 is attached to the needle hub 22 and the distal end of the guide wire 80 is positioned inside the distal end portion of the inner needle 20, the most distal end portion of the extension portion 186 is positioned on the distal end side of the most proximal end portion of the needle hub 22. With this configuration, it is easy to operate the wire operation member 170.

In the present embodiment, the guide member 168 is provided with the guide rail 178 that axially overlaps the needle hub 22 in the state where the guide member 168 is attached to the needle hub 22 and slidably supports and guides the extension portion 186 in the axial direction. With this configuration, it is possible to improve stability in straight movement of the wire operation member 170.

In the present embodiment, the needle hub 22 is provided with the guide rib 174 (see FIG. 29) that slidably supports and guides the extension portion 186 in the axial direction at the time of moving the wire operation member 170 forward with respect to the needle hub 22 in order to cause the distal end of the guide wire 80 to protrude from the distal end of the inner needle 20 by the predetermined length. With this configuration, it is possible to improve stability in straight movement of the wire operation member 170.

In the present embodiment, the guide member 168 is provided with the guide wire retraction inhibition mechanism (the bulging portion 196; see FIG. 32) that inhibits the wire operation member 170 from retracting with respect to the needle hub 22 after the guide wire 80 moves forward such that the guide wire 80 protrudes from the distal end of the inner needle 20 by the predetermined length. With this configuration, it is possible to smoothly perform the insertion of the guide wire 80.

In the present embodiment, the guide member 168 is formed to be longer than the guide wire 80, and the entire length of the guide wire 80 is housed in the guide member 168 in the initial state. Instead of this configuration, the guide member 168 may be configured to be shorter than the guide wire 80 such that the guide wire 80 is exposed to the front from the guide member 168 for a long time in a state before the guide wire unit 172 is attached to the catheter unit 12.

In the present embodiment, since the guide wire 80 is fixed to the wire operation member 170, the guide wire 80 moves by the same moving distance as the wire operation member 170 at the time of operating the wire operation member 170 in the axial direction. Instead of this configuration, the wire operation member 170 and the guide wire 80 may be arranged and configured such that the guide wire 80 moves by an integral multiple of a moving distance of the wire operation member 170.

Incidentally, a cover 200 that covers the guide wire 80 may be attached to the guide member 168 as illustrated by an imaginary line in FIG. 28. Accordingly, it is possible to inhibit contamination of the guide wire 80.

As illustrated in FIG. 34, a convex portion 198 serving as a reference position may be provided on a side surface of the needle hub 22, and the rib 190 provided as an anti-slip mechanism on the wire operation member 170 may function as a marking to know a protrusion length of the guide wire 80 from the distal end of the inner needle 20. In this case, it is possible to grasp the protrusion length of the guide wire 80 from the distal end of the inner needle 20 by viewing a positional relationship between the convex portion 198 and the rib 190.

Figure 36:
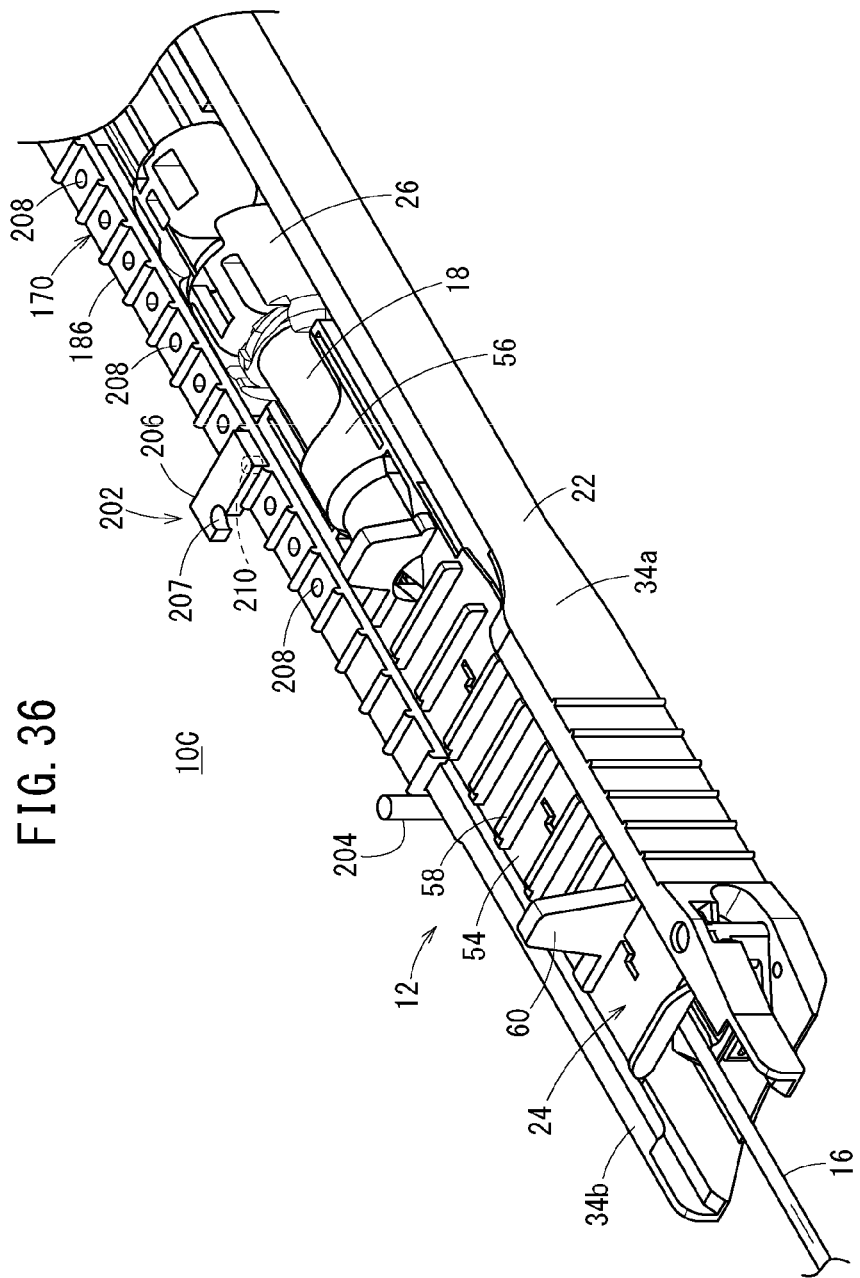
FIG. 36 is a perspective view illustrating a modification in which a catheter unit is provided with an excessive insertion inhibition mechanism.

As illustrated in FIG. 36, the guide wire unit 172 may be provided with an excessive insertion inhibition mechanism 202 that inhibits excessive insertion of the guide wire 80. The excessive insertion inhibition mechanism 202 has a first element 204 protruding from the needle hub 22 and a second element 206 protruding from the extension portion 186. As the second element 206 is locked to the first element 204 along with forward movement of the wire operation member 170 with respect to the needle hub 22, the movement of the wire operation member 170 in the distal end direction with respect to the needle hub 22 is inhibited.

The second element 206 may be configured to be fixable to the extension portion 186 at an arbitrary position by the user. In this case, for example, the extension portion 186 is provided with a plurality of connection holes 208 along the longitudinal direction, and a connection convex portion 210 selectively fittable to these connection holes 208 Is provided on a lower surface of the second element 206. The user can arbitrarily set the protrusion length of the guide wire 80 by selecting a position where the second element 206 is attached to the extension portion 186.

In addition, the excessive insertion inhibition mechanism 202 may be configured such that the first element 204 and the second element 206 are engaged and locked when the guide wire 80 moves forward. In this case, for example, the first element 204 is formed in a columnar shape, and the second element 206 is formed with an arcuate groove 207 to which the first element 204 can be fitted as illustrated in FIG. 36. With this excessive insertion inhibition mechanism 202, it is possible to inhibit unintentional retraction of the guide wire 80 having protruded from the distal end of the inner needle 20 by the predetermined length.

The present invention is not limited to the above-described embodiments, and various modifications can be made within a scope not departing from the spirit of the present invention.

What is claimed is:

1. A catheter assembly comprising:
    a catheter;
    a hollow inner needle that is removably disposed in the catheter and has a lumen through which a guide wire is insertable;
    a needle hub that is fixed to a proximal end portion of the inner needle; and
    a guide member that is attachable to a proximal end portion of the needle hub and configured to guide the guide wire towards the inner needle,
    wherein the needle hub comprises:
        left and right sidewalls,
        a needle holding portion that is disposed between the left and right sidewalls and holds the proximal end portion of the inner needle, and
        a plurality of first fitting portions disposed at the proximal end portion of the needle hub, the plurality of first fitting portions being formed of the left and right sidewalls and the needle holding portion,
    wherein the guide member comprises a plurality of second fitting portions disposed at a distal end portion of the guide member, the plurality of second fitting portions being fittable to the plurality of first fitting portions.

2. The catheter assembly according to claim 1, further comprising:
    the guide wire, which is slidably supported on the guide member; and
    a wire operation member that supports the guide wire, is relatively displaceable in an axial direction with respect to the guide member, and is configured to move the guide wire in the axial direction with respect to the guide member along with displacement of the wire operation member.

3. The catheter assembly according to claim 2, further comprising:
    a cover that has a hollow cylindrical shape, the cover being configured to cover the guide wire between the guide member and the wire operation member in an initial state, and to contract in the axial direction along with movement of the wire operation member in a distal end direction with respect to the guide member.

4. The catheter assembly according to claim 3, wherein:
    the wire operation member is relatively movable in the axial direction within a regulated range with respect to the cover, and
    a distal end of the guide wire is positioned in the lumen of a distal end portion of the inner needle in a state in which the guide member is attached to the needle hub, the cover contracts in the axial direction to a maximum extent, and the wire operation member is positioned on a most proximal end side with respect to the cover.

5. The catheter assembly according to claim 3, wherein:
    the cover comprises a lock mechanism that fixes the cover to the guide member when the cover contracts in the axial direction to a maximum extent.

6. The catheter assembly according to claim 3, wherein:
    the cover has a telescopic structure in which a plurality of tubular members having different sizes are combined so as to be relatively movable in the axial direction.

7. The catheter assembly according to claim 2, wherein:
    the wire operation member is supported so as to be slidable in the axial direction by the guide member.

8. The catheter assembly according to claim 7, wherein:
    the wire operation member comprises:
        a slide portion engaged with the guide member so as to be slidable in the axial direction, and
        an extension portion extending from the slide portion in a distal end direction, and
        a most distal end portion of the extension portion is positioned on a distal end side of a most proximal end portion of the needle hub in a state in which the guide member is attached to the needle hub and a distal end of the guide wire is positioned inside a distal end portion of the inner needle.

9. The catheter assembly according to claim 8, wherein:
    the guide member comprises a guide rail that overlaps the needle hub in the axial direction in a state in which the guide member is attached to the needle hub, the guide rail being configured to slidably support the extension portion and to guide the extension portion in the axial direction.

10. The catheter assembly according to claim 1, wherein:
    the guide member has a guide groove configured to guide the guide wire toward the lumen of the inner needle, and the guide groove comprises:
- a bottom portion extending coaxially with the lumen of the inner needle in a state in which the guide member is attached to the needle hub, and
- a inducing portion that is open on an upper surface of the guide member, is continuous to the bottom portion, and is narrowed in width toward the bottom portion.

11. The catheter assembly according to claim 10, further comprising:
a retraction inhibition portion that is fixed to the guide wire and inhibits the guide wire from retracting with respect to the needle hub after the guide wire moves forward such that the guide wire protrudes from the distal end of the inner needle by a predetermined length.

12. The catheter assembly according to claim 1, wherein:
the plurality of first fitting portions are female fitting portions that are open in a proximal end direction, and
the plurality of second fitting portions are male fitting portions that protrude in a distal end direction.

13. The catheter assembly according to claim 12, wherein:
each of the plurality of first fitting portion comprises a first sidewall surface, and a concave portion that is disposed on the first sidewall surface and extends in an axial direction, and
each of the plurality of second fitting portions comprises a second sidewall surface and a convex portion that is disposed on the second sidewall surface, extends in the axial direction, and is fittable to a respective concave portion.

14. The catheter assembly according to claim 1, wherein:
the needle hub has a wire introduction hole that communicates with the lumen of the inner needle on a proximal end side of the inner needle and through which the guide wire is insertable,
the guide member has a wire lead-out hole through which the guide wire is insertable, and
one or both of the wire introduction hole and the wire lead-out hole are formed in a tapered shape that decreases in diameter toward the inner needle.

* * * * *